United States Patent
Ladram et al.

(10) Patent No.: US 9,932,376 B2
(45) Date of Patent: Apr. 3, 2018

(54) ANALOGUES OF TEMPORIN-SHA AND USES THEREOF

(71) Applicants: UNIVERSITE PIERRE ET MARIE CURIE (PARIS 6), Paris (FR); INSTITUT DE RECHERCHE POUR LE DEVELOPPEMENT, Marseilles (FR)

(72) Inventors: Ali Ladram, Ermont (FR); Denis Sereno, Poussan (FR); Thierry Foulon, Paris (FR); Bruno Oury, Vendargues (FR)

(73) Assignees: INSTITUT DE RECHERCHE POUR LE DEVELOPPEMENT, Marseille (FR); UNIVERSITE PIERRE ET MARIE CURIE (PARIS 6), Paris (FR)

( * ) Notice: Subject to any disclaimer, the term of this patent is extended or adjusted under 35 U.S.C. 154(b) by 0 days.

(21) Appl. No.: 15/021,948

(22) PCT Filed: Sep. 26, 2014

(86) PCT No.: PCT/EP2014/070633
§ 371 (c)(1),
(2) Date: Mar. 15, 2016

(87) PCT Pub. No.: WO2015/044356
PCT Pub. Date: Apr. 2, 2015

(65) Prior Publication Data
US 2016/0280749 A1    Sep. 29, 2016

(30) Foreign Application Priority Data

Sep. 27, 2013  (EP) ..................................... 13306344

(51) Int. Cl.
C07K 14/46     (2006.01)
A61K 38/00     (2006.01)

(52) U.S. Cl.
CPC ............ *C07K 14/463* (2013.01); *A61K 38/00* (2013.01)

(58) Field of Classification Search
None
See application file for complete search history.

(56) References Cited

U.S. PATENT DOCUMENTS

| | | |
|---|---|---|
| 5,789,382 A | 8/1998 | Wellstein |
| 5,916,872 A | 6/1999 | Chang et al. |
| 9,522,942 B2 | 12/2016 | Ladram et al. |
| 2012/0005790 A1 | 1/2012 | Ladram et al. |

FOREIGN PATENT DOCUMENTS

WO     WO 2010/106293    9/2010

OTHER PUBLICATIONS

Abbassi, F. et al. "Isolation, characterization and molecular cloning of new temporins from the skin of the North African ranid *Pelophylax saharica*" Peptides, Sep. 1, 2008, pp. 1526-1533, vol. 29, No. 9.
Written Opinion in International Application No. PCT/EP2014/070633, dated Jan. 27, 2015, pp. 1-6.
Conlon, J. Michael. et al. "Strategies for transformation of naturally-occurring amphibian antimicrobial peptides into therapeutically valuable anti-infective agents" Methods, 2007, pp. 349-357, vol. 42, XP-002547419.
Dennison, S. R. et al. "Amphiphilic α-Helical Antimicrobial Peptides and Their Structure/Function Relationships" Protein and Peptide Letters, 2005, pp. 31-39, vol. 12, XP-008112284.
Abbassi, F. et al. "Solution Structure and Model Membrane Interactions of Temporins-Sh, Antimicrobial Peptides from Amphibian Skin. A NMR Spectroscopy and Differential Scanning Calorimetry Study" Biochemistry, 2008, pp. 10513-10525, vol. 47, XP-002547417.
Conlon, J. Michael et al. "Antimicrobial peptides from the skins of North American frogs" Biochimica et Biophysica Acta, 2009, pp. 1556-1563, vol. 1788, No. 8, XP-002547418.
Giangaspero, A. et al. "Amphipathic α helical antimicrobial peptides" Eur. J. Biochem, 2001, pp. 5589-5600, vol. 268, XP-002547420.
Mangoni, M. L. "Temporins, anti-infective peptides with expanding properties" Cell. Mol. Life Sci., 2006, pp. 1060-1069, vol. 63, XP-19419142.
Written Opinion in International Application No. PCT/FR2010/050487, dated Aug. 31, 2010, pp. 1-6.
Wells, J. A. "Additivity of Mutational Effects in Proteins" Biochemistry, Sep. 18, 1990, pp. 8509-8517, vol. 29, No. 37.
Ngo, J. T. et al. "Computational Complexity, Protein Structure Prediction, and the Levinthal Paradox" The Protein Folding Problem and Tertiary Structure Prediction, 1994, pp. 491-495.
Guo, H. H. et al. "Protein tolerance to random amino acid change" PNAS, Jun. 22, 2004, pp. 9205-9210, vol. 101, No. 25.
Keskin, O. etal. "A new, structurally nonredundant, diverse data set of protein-protein interfaces and its implications" Protein Sciences, 2004, pp. 1043-1055, vol. 13.
Thornton, J. M. et al. "From structure to function: Approaches and limitations" Nature Structural Biology—Structural Genomics Supplement, Nov. 2000, pp. 991-994.
Uniprot, Accession No. B3KYH4_PELSA, 2008, pp. 1-2.
Nagpal, S. et al. "Plasticity in structure and interactions is critical for the action of indolicidin, an antibacterial peptide of innate immune origin" Protein Science, 2002, pp. 2158-2167, vol. 11.
Chorev, M. et al. "Recent developments in retro peptides and proteins —an ongoing topochemical exploration" Tibtech, Oct. 1995, pp. 438-445, vol. 13.

*Primary Examiner* — Christina Bradley
(74) *Attorney, Agent, or Firm* — Saliwanchik, Lloyd & Eisenschenk

(57) ABSTRACT

The present invention relates to novel antimicrobial peptides, pharmaceutical compositions comprising said peptides, and the uses thereof, in particular as antimicrobial drugs, disinfectants, pesticides or preservatives. The present invention also relates to a transgenic plant expressing said novel peptides.

22 Claims, 4 Drawing Sheets

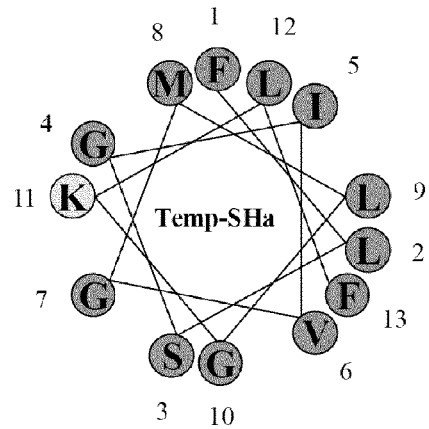

Figure 1

| Peptide of the invention<br>Abbreviation used | Sequence | <H> | <µH> | Net charge |
|---|---|---|---|---|
| Temporin-SHa<br>*SHa* | FLSGIVGMLGKLF<sub>a</sub><br>(SEQ ID NO: 1) | 3.46 | 0.72 | + 2 |
| [K³]temporin-SHa<br>*K³* | FLKGIVGMLGKLF<sub>a</sub><br>(SEQ ID NO: 29) | 3.03 | 0.78 | + 3 |
| [K³]temporin-SHa(3-13)<br>*K³(3-13)* | --KGIVGMLGKLF<sub>a</sub><br>(SEQ ID NO: 30) | 1.79 | 0.74 | + 3 |
| [K³,K⁶]temporin-SHa<br>*[K³,K⁶]* | FLKGIKGMLGKLF<sub>a</sub><br>(SEQ ID NO: 3) | 1.96 | 0.77 | + 4 |
| [K³,K⁸]temporin-SHa<br>*[K³,K⁸]* | FLKGIVGKLGKLF<sub>a</sub><br>(SEQ ID NO: 4) | 1.92 | 0.76 | + 4 |
| [K³,L¹³]temporin-SHa<br>*[K³,L¹³]* | FLKGIVGMLGKLL<sub>a</sub><br>(SEQ ID NO: 5) | 3.01 | 0.77 | + 3 |
| [K³,K⁶,L¹³]temporin-SHa<br>*[K³,K⁶,L¹³]* | FLKGIKGMLGKLL<sub>a</sub><br>(SEQ ID NO: 8) | 1.93 | 0.76 | + 4 |
| [K³,W¹³]temporin-SHa<br>*[K³,W¹³]* | FLKGIVGMLGKLW<sub>a</sub><br>(SEQ ID NO: 6) | 3.01 | 0.77 | + 3 |

Figure 2

|  | SHa | K³ | K³(3-13) |
|---|---|---|---|
| Gram-negative bacteria (MIC, µM) | | | |
| E. coli ATCC 25922 | 10 | 3 | 30 |
| E. coli ML-35p | 12 | 3 | 25 |
| P. aeruginosa ATCC 27853 | 50 | 6 | 25 |
| S. enterica (serotype Enteritidis) | 25 | 6 | 100 |
| A. baumannii ATCC 19606 | 6 | 3 | 50 |
| K. pneumoniae ATCC 13883 | 12 | 3 | 100 |
| Gram-positive bacteria (MIC, µM) | | | |
| S. aureus ATCC 25923 | 3 | 3 | 40 |
| S. aureus ST1065 | 6 | 3 | 40 |
| S. aureus ATCC 43300[a] | 6 | 3 | ND |
| S. aureus ATCC BAA-44[b] | 6 | 3 | ND |
| S. pyogenes ATCC 19615 | 6 | 1 | 50 |
| Listeria ivanovii | 6 | 3 | 12 |
| E. faecalis ATCC 29212 | 12 | 6 | > 200 |
| Yeasts (MIC, µM) | | | |
| C. albicans ATCC 90028 | 25 | 6 | 12 |
| C. parapsilosis ATCC 22019 | 100 | 25 | 50 |
| S. cerevisiae | 12 | 3 | 12 |
| Leishmania parasites (IC50, µM) | | | |
| Promastigotes L. infantum | 18 | 10 | 90 |
| Cells (IC$_{50}$ or LC$_{50}$, µM) | | | |
| Rat erythrocytes (LC$_{50}$, µM) | 25 | 26 | 618 |
| Human THP-1 monocytes (IC$_{50}$, µM) | > 60 | 48 | ND |
| Human THP-1 macrophages (LC$_{50}$, µM) | > 60 | 47 | ND |
| HepG2 (LC$_{50}$, µM) | 560 | 358 | ND |
| Human fibroblasts (LC$_{50}$, µM) | > 100 | > 100 | ND |

Figure 4

|  | $K^3,K^6$ | $K^3,K^8$ | $K^3,L^{13}$ | $K^3,K^6,L^{13}$ | $K^3,W^{13}$ |
|---|---|---|---|---|---|
| Gram-negative bacteria (MIC, µM) | | | | | |
| E. coli ATCC 25922 | 12 | 12 | 6 | 12 | 3 |
| E. coli ML-35p | 3 | 6 | 3 | 6 | 3 |
| P. aeruginosa ATCC 27853 | 12 | 12 | 12 | 12 | 6 |
| S. enterica (serotype Enteritidis) | 50 | 25 | 6 | 50 | 6 |
| A. baumannii ATCC 19606 | 25 | 25 | 6 | 25 | 6 |
| K. pneumoniae ATCC 13883 | 25 | 25 | 6 | 50 | 3 |
| Gram-positive bacteria (MIC, µM) | | | | | |
| S. aureus ATCC 25923 | 6 | 6 | 3 | 12 | 3 |
| S. aureus ST1065 | 6 | 6 | 3 | 12 | 3 |
| S. pyogenes ATCC 19615 | 3 | 3 | 3 | 6 | 3 |
| Listeria ivanovii | 6 | 12 | 3 | 12 | 3 |
| E. faecalis ATCC 29212 | 50 | 50 | 12 | 100 | 6 |
| Yeasts (MIC, µM) | | | | | |
| C. albicans ATCC 90028 | 12 | 12 | 6 | 12 | 6 |
| C. parapsilosis ATCC 22019 | 25 | 25 | 25 | 50 | 50 |
| S. cerevisiae | 6 | 6 | 3 | 6 | 6 |
| Leishmania parasites (IC50, µM) | | | | | |
| Promastigotes L. infantum | 57 | 46 | 28 | 56 | 26 |
| Cells (IC$_{50}$ or LC$_{50}$, µM) | | | | | |
| Rat erythrocytes (LC$_{50}$, µM) | 590 | 530 | 45 | > 800 | 32 |
| Human THP-1 monocytes (IC$_{50}$, µM) | 55 | 60 | ND | 51 | ND |
| Human THP-1 macrophages (LC$_{50}$, µM) | ND | ND | 61 | ND | 25 |
| HepG2 (LC$_{50}$, µM) | ND | ND | 376 | 295 | ND |
| Human fibroblasts (LC$_{50}$, µM) | ND | ND | ND | ND | ND |

Figure 5

ANALOGUES OF TEMPORIN-SHA AND USES THEREOF

CROSS-REFERENCE TO RELATED APPLICATION

This application is the U.S. national stage application of International Patent Application No. PCT/EP2014/070633, filed Sep. 26, 2014.

The Sequence Listing for this application is labeled "Seq-List-replace.txt" which was created on Jun. 10, 2016 and is 12 KB. The entire content of the sequence listing is incorporated herein by reference in its entirety.

FIELD OF THE INVENTION

The present invention relates to novel antimicrobial peptides, pharmaceutical compositions comprising said peptides and the uses thereof, in particular as a medicament, disinfectant, preservative, pesticide or agent preventing biofilm formation.

TECHNOLOGICAL BACKGROUND OF THE INVENTION

The evolution and spread of antibiotic resistance among bacteria is a major public health problem today, especially in the hospital setting with the emergence of multidrug resistant strains. Intensive research efforts have led to the development of new antibiotics effective against these resistant strains. Nevertheless, through use, mechanisms of resistance to these drugs emerge and limit their efficacy.

In view of this phenomenon, antimicrobial peptides (AMP) appear very promising for the design of new therapeutic agents. Cationic antimicrobial peptides are thought to be one of the key components of the innate immune system of multicellular organisms, which provides first-line defense against pathogens. The interest of these peptides lies on the one hand in their very broad spectrum of activity, enabling in particular their use in the treatment of infections caused by multidrug resistant strains. Secondly, their mode of action is based on permeabilization or rapid fragmentation of the microorganism membrane and is therefore unlikely to lead to the development of resistance mechanisms.

In particular, AMP have attracted considerable interest as potential agents against bacterial biofilms. Biofilms are bacteria that stick together, forming a community, which is embedded within a self-produced matrix. Biofilm bacteria show much greater resistance to antibiotics than their free-living counterparts and are responsible for various pathological conditions that are difficult to treat, such as chronic infection of patients affected with cystic fibrosis, endocarditis, and cystitis, infections caused by indwelling medical devices and dental plaque formation involved in caries and periodontitis. Since biofilm resistance to antibiotics is mainly due to the slow growth rate and low metabolic activity of bacteria in such communities, the use of AMP appears to be an attractive therapeutic approach because, due to their mode of action, they have a high potential to act also on slow growing or even non-growing bacteria. Antimicrobial peptides have been identified in plants, insects, amphibians and mammals. Amphibian skin represents a major source of antimicrobial peptides and every species of frog possesses its specific peptide repertoire generally composed of 10 to 15 AMP.

Frogs of the Ranidae family are very numerous and this family currently includes 16 genera and 338 species. These frogs synthesize and secrete a remarkable diversity of AMP, which have been classified into 13 families (Conlon et al., 2008 and 2009). One such family, the temporins, comprises AMP of small size (generally between 10 and 14 residues), the sequences of which vary widely according to species. More than 100 members of the temporin family have been identified. These temporins have been isolated from several *Rana* species such as *Rana temporaria* (Simmaco et al., 1996), *Rana esculenta* (Simmaco et al., 1990), *Rana japonica* (Isaacson et al., 2002), *Rana ornativentris* (Kim et al., 2001) and *Pelophylax* (*Rana*) *saharica* (Abbassi et al., 2008; Abbassi et al., 2010; Abbassi et al., 2013).

Unlike the other 12 families of Ranidae peptides, the temporins lack the "*Rana* box" motif, a C-terminal heptapeptide domain cyclized by a disulfide bridge (Mangoni, 2006). Furthermore, the majority of temporins contain a single basic residue, which confers a net charge of +2 at physiological pH. Generally, the temporins are particularly active against Gram-positive bacteria and yeasts but they also exhibit antifungal properties (Rollins-Smith et al., 2003) and, for some, antiviral properties (Chinchar et al., 2004).

It was found that temporin-SHa isolated from the skin of the North African frog *Pelophylax saharica* exhibits antiparasitic activity against protozoa belonging to the genus *Leishmania*, which are the causal agents of leishmaniosis (Abbassi et al., 2008). Based on this finding, analogues of said temporin exhibiting improved antimicrobial activity were obtained by substitution of one or more amino acids of the polar face of the α helix by a basic amino acid (WO 2010/106293). However, their toxicity, and in particular their hemolytic activity, constitutes an obstacle to their therapeutic uses, in particular if they are to be administered systematically.

Therefore, there is still a great need for improved antimicrobial peptides exhibiting strong antimicrobial activity and greatly reduced toxicity against mammalian cells.

SUMMARY OF THE INVENTION

The invention aims to provide novel antimicrobial peptides, analogues of temporin-SHa exhibiting increased antimicrobial activity and reduced hemolytic activity.

Accordingly, the present invention relates to a peptide of a size comprised between 13 and 100 amino acids, exhibiting an antimicrobial activity and comprising the sequence F-L-$X_1$-G-I-$X_2$-G-$X_3$-L-G-K-L-$X_4$ (SEQ ID NO: 2), wherein $X_1$ is an amino acid selected from the group consisting of R, H and K, $X_2$ is an amino acid selected from the group consisting of V, R, H and K, $X_3$ is an amino acid selected from the group consisting of M, R, H and K, and $X_4$ is an amino acid selected from the group consisting of F, L, I and W, with the proviso that when $X_2$ is V, then $X_3$ is selected from the group consisting of K, R and H and/or $X_4$ is selected from the group consisting of L, I and W, and the functional derivatives and pharmaceutically acceptable salts of said peptide.

Preferably, $X_1$ represents K, $X_2$ is an amino acid selected from the group consisting of V and K, $X_3$ is an amino acid selected from the group consisting of M and K, and $X_4$ is an amino acid selected from the group consisting of F, L and W.

In particular, the peptide may be selected from the group consisting of peptides comprising, or consisting of, a sequence selected from the group consisting of:
F-L-K-G-I-K-G-M-L-G-K-L-F (SEQ ID NO: 3),
F-L-K-G-I-V-G-K-L-G-K-L-F (SEQ ID NO: 4),
F-L-K-G-I-V-G-M-L-G-K-L-L (SEQ ID NO: 5), F-L-K-G-I-V-G-M-L-G-K-L-W (SEQ ID NO: 6),
F-L-K-G-I-V-G-M-L-G-K-L-I (SEQ ID NO: 7)
F-L-K-G-I-K-G-M-L-G-K-L-L (SEQ ID NO: 8),
F-L-K-G-I-K-G-M-L-G-K-L-W (SEQ ID NO: 9),
F-L-K-G-I-K-G-M-L-G-K-L-I (SEQ ID NO: 10),
F-L-K-G-I-V-G-K-L-G-K-L-W (SEQ ID NO: 11),
F-L-K-G-I-V-G-K-L-G-K-L-L (SEQ ID NO: 12),
F-L-K-G-I-V-G-K-L-G-K-L-I (SEQ ID NO: 13),
F-L-K-G-I-K-G-K-L-G-K-L-F (SEQ ID NO: 14),
F-L-K-G-I-K-G-K-L-G-K-L-L (SEQ ID NO: 15),
F-L-K-G-I-K-G-K-L-G-K-L-W (SEQ ID NO: 16), and
F-L-K-G-I-K-G-K-L-G-K-L-I (SEQ ID NO: 17).

Preferably, the peptide comprises, or consists of, a sequence selected from the group consisting of the sequences of SEQ ID NOs: 3 to 6, 8, 9, 11, 12 and 14 to 16. More preferably, the peptide comprises, or consists of, a sequence selected from the group consisting of the sequences of SEQ ID NOs: 3 to 6 and 8, and even more preferably from the group consisting of the sequences of SEQ ID NOs: 3, 5 and 6.

In another aspect, the present invention relates to a nucleic acid coding for a peptide according to the invention, or an expression cassette or expression vector comprising said nucleic acid. The present invention further relates to a host cell comprising said nucleic acid, expression cassette or expression vector.

The present invention also relates to an antibody specifically binding to a peptide according to the invention.

In a further aspect, the present invention relates to a pharmaceutical composition comprising at least one peptide according to the invention, and a pharmaceutically acceptable support and/or excipient.

The present invention further relates to a peptide according to the invention, as a medicament. Preferably, the medicament is intended for treating an infection caused by a bacterium, virus, fungus or parasite. Preferably, the parasite belongs to the genus *Leishmania* and preferably is *Leishmania infantum*.

In still another aspect, the present invention relates to the use of a peptide according to the invention as a disinfectant, preservative or pesticide.

In another aspect, the present invention relates to a medical device or implant comprising a body having at least one surface coated with or including a peptide according to the invention.

In a final aspect, the present invention relates to a transgenic plant comprising a nucleic acid, cassette or expression vector according to the invention, and able to express or expressing a peptide according to the invention.

BRIEF DESCRIPTION OF DRAWINGS

FIG. 1: Schiffer-Edmunson projection of the α helix of temporin-SHa. Residues 4, 11, 7, 3 and 10 constitute the polar face of the helix. Residues 8, 1, 12, 5, 9, 2, 13 and 6 constitute the apolar face of the helix.

FIG. 2: Primary structure and physicochemical properties of temporin-SHa and analogues. All peptides are amidated at the C-terminus (a). Modifications (substitution and deletion) of amino acid residues are indicated in bold in relation to the parent peptide temporin–SHa. Bold horizontal lines correspond to deletions (–). The net charge was calculated at pH 7.4. The mean hydrophobicity (<H>) and the mean relative hydrophobic moment (<μH>) were calculated with the CCS scale (Combined Consensus hydrophobicity Scale) using HydroMCalc (see Worldwide Website: bbcm.univ.trieste.it/~tossi/HydroCalc/HydroMCalc.html).

FIG. 4: Antimicrobial and cytotoxic activities of temporin-SHa and substituted or truncated analogues of temporin-SHa. The activity against antibiotic-resistant *Staphylococcus aureus* strains (*S. aureus* ATCC 43300 and ATCC BAA-44) is also indicated. ND: not determined. a: resistant to methicillin and oxacillin. b: resistant to methicillin, amoxicillin/clavulanic acid, cephalothin, ciprofloxacin, erythromycin, gentamicin, imipenem, oxacillin, penicillin, tetracycline, ampicillin, doxycycline, azithromycin, ceftriaxone, clindamycin, lincomycin, perfloxacin, rifampin, and tobramycin.

FIG. 5: Antimicrobial and cytotoxic activities of substituted analogues of temporin-SHa. ND: not determined.

DETAILED DESCRIPTION OF THE INVENTION

Figure 3:
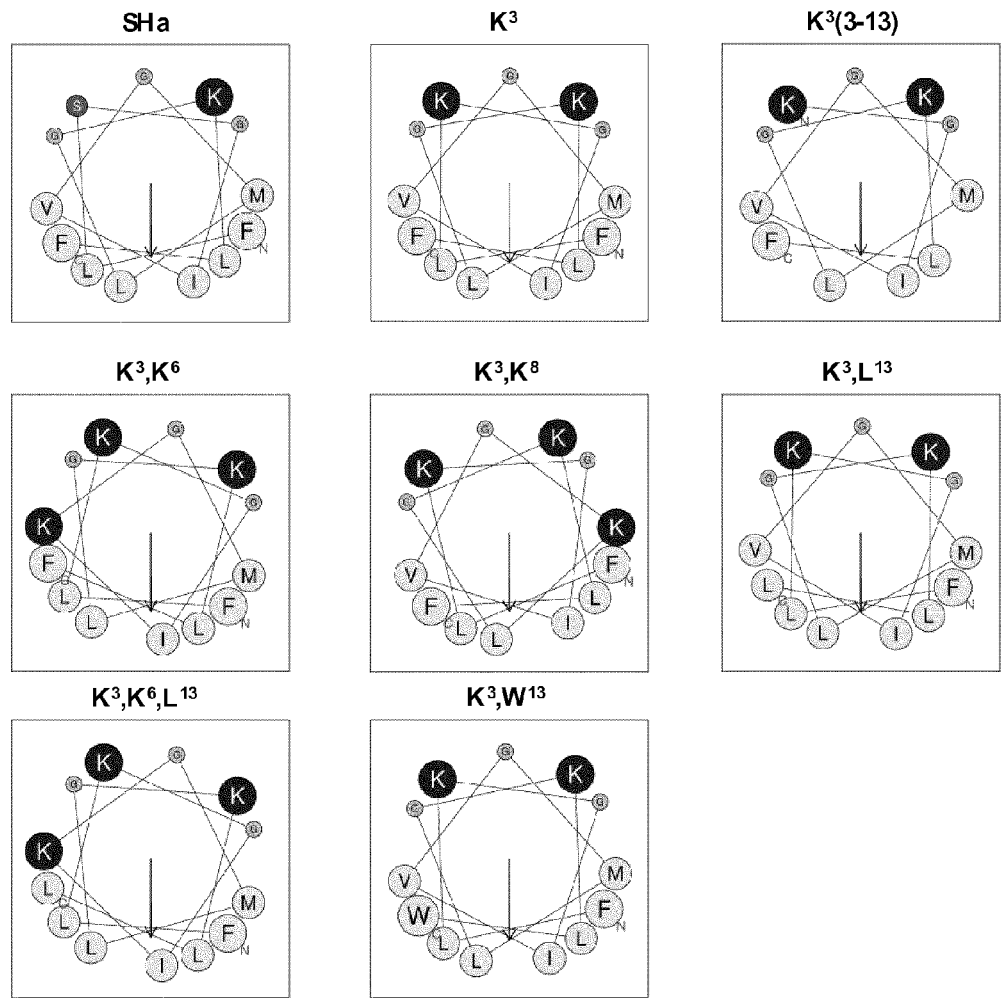
FIG. 3: Schiffer-Edmundson projection of temporin-SHa and analogues of the invention. Helical wheels were drawn using HeliQuest (http://heliquest.ipmc.cnrs.fr). "N" and "C" represent N-terminus and C-terminus, respectively. Non-polar and polar/neutral/charged residues are shown and circled proportionally to amino acid volume. The hydrophobic moment vector (<μH>) is also indicated (arrow). All peptides clearly adopt an amphipathic structure with two well-separated clusters of hydrophobic and hydrophilic/basic residues located on opposing sides of the helical wheel.

Temporin-SHa, formerly known as temporin-1Sa, was isolated from the skin of the North African frog *Pelophylax saharica* (Abbassi et al., 2008). This temporin is obtained by post-translational maturation of a 50-residue precursor (GenBank database number: CAO77282). This precursor has a highly conserved N-terminal domain containing the signal peptide and a region rich in acidic residues, as well as a hypervariable C-terminal domain containing the temporin-SHa progenitor sequence. In vivo, the mature form of temporin is obtained after i) proteolytic cleavage of the KR doublet which precedes the progenitor sequence, ii) elimination of the C-terminal K residue from the progenitor sequence by the action of a carboxypeptidase, and iii) amidation of the C-terminal residue of temporin by the C-terminal G residue of the progenitor sequence which serves as amide group donor (substrate of peptidyl-glycine α-amidating monooxygenase). The mature protein is a peptide of 13 amino acids in length and having the sequence F-L-S-G-I-V-G-M-L-G-K-L-F (SEQ ID NO: 1). Temporins are unstructured in aqueous solution but adopt an α helical structure in membrane-mimetic environments.

Said peptide exhibits antimicrobial activity against Gram-positive and Gram-negative bacteria, yeasts, and the parasite *Leishmania infantum* (Abbassi et al., 2008). The antiparasitic action of temporin-SHa occurs against both the promastigote and axenic amastigote forms of the parasite with an $IC_{50}$ of 18.1 μM and 22.8 respectively.

The main problem in optimizing AMPS is that their antimicrobial and cytolytic activities reflect a subtle equilibrium between several parameters including cationicity, hydrophobicity, α-helicity and amphipathicity (Giangaspero et al., 2001; Yeaman et al., 2003; Dennison et al., 2005). These parameters are very closely linked and the mere substitution of an amino acid residue can induce a simultaneous modification of several physicochemical properties of the peptide (Conlon et al., 2007).

In previous studies, the inventors found that the substitution of one or more amino acids of the polar face of the α helix of temporin-SHa by a basic amino acid leads to analogues of said temporin having increased antimicrobial activity. In particular, they demonstrated that the substitution of residue 3 of temporin-SHa of SEQ ID NO: 1 by a basic amino acid, i.e., H, R or K, increases activity against Gram+ and Gram− bacteria, yeasts and *Leishmania infantum*.

They have herein shown, in a surprising manner, that the further substitution of one or more amino acids of the apolar face of the α helix of said temporin-SHa analogue greatly reduces cytolytic activity while preserving antimicrobial activity.

Definitions

Herein, the terms "peptide", "oligopeptide", "polypeptide" and "protein" are employed interchangeably and refer to a chain of amino acids linked by peptide bonds, regardless of the number of amino acids forming said chain.

In the peptide sequences described herein, the amino acids are represented by their one-letter code according to the following nomenclature: C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophan; and Y: tyrosine.

The term "substitution", as used herein in relation to a position or amino acid, means that the amino acid in the particular position has been replaced by another amino acid or that an amino acid different from the one of the wild-type peptide (SEQ ID NO: 1) is present.

The term "conservative substitution" as employed herein refers to a substitution of an amino acid residue by another, which has similar chemical or physical properties (size, charge or polarity). As an example, isoleucine, leucine, alanine and valine may be mutually conservatively substituted, just like (i) lysine, histidine and arginine, (ii) serine and threonine, (iii) cysteine and methionine, (iv) asparagine and glutamine, (v) tryptophan, tyrosine and phenylalanine or (vi) aspartic acid and glutamic acid.

The terms "microbe" or "microbial" as employed herein refer to bacteria, fungi, yeasts, viruses and/or parasites.

The term "microbial infection" as employed herein refers to an infection caused by bacteria, fungi, yeasts, viruses and/or parasites.

The term "antimicrobial activity" as employed herein refers to an antibacterial, antiviral, antifungal and/or antiparasitic activity. Said activity may be evaluated by measuring different parameters such as $IC_{50}$ or MIC.

"$IC_{50}$" or "half maximal inhibitory concentration" is the concentration of a substance needed to reduce the growth in vitro of a population of microorganisms by half.

"MIC" or "minimum inhibitory concentration" is the lowest concentration of a substance that will totally inhibit microbial growth after 18 hours of incubation, generally at 37° C., in the presence of said substance.

The term "lethal concentration, 50%" or "$LC_{50}$" as employed herein refers to the concentration of a substance required to kill half a population. $LC_{50}$ is a quantitative indicator of the toxicity of a substance. In particular, $LC_{50}$ is employed herein to evaluate the cytolytic activity of AMP and in this case corresponds to the concentration of a peptide inducing lysis of half the cell population.

In a first aspect, the present invention relates to a peptide analogue of temporin-SHa in which residue 3 of the polar face and residues 6, 8 and/or 13 of the apolar face of the α helix are substituted (see FIGS. 1 and 2). In particular, in said analogue, residues 3, 6 and/or 8 are substituted by basic amino acid.

The present invention therefore relates to a peptide analogue of temporin-SHa exhibiting an antimicrobial activity and comprising, or consisting of, the sequence F-L-$X_1$-G-I-$X_2$-G-$X_3$-L-G-K-L-$X_4$ (SEQ ID NO: 2), wherein $X_1$ is an amino acid selected from the group consisting of R, H and K, $X_2$ is an amino acid selected from the group consisting of V, R, H and K, $X_3$ is an amino acid selected from the group consisting of M, R, H and K, and $X_4$ is an amino acid selected from the group consisting of F, L, I and W, with the proviso that when $X_2$ is V, then $X_3$ is selected from the group consisting of K, R and H and/or $X_4$ is selected from the group consisting of L, I and W, and the functional derivatives and pharmaceutically acceptable salts of said peptide.

In a particular embodiment, when $X_1$ is K, $X_2$ is V and $X_3$ is K, then $X_4$ is selected from the group consisting of L, I and W, and when $X_1$ is K, $X_2$ is K and $X_3$ is M, then $X_4$ is selected from the group consisting of F, I and W.

Preferably, $X_1$ represents K, $X_2$ is selected from the group consisting of V and K, $X_3$ is selected from the group consisting of M and K, and $X_4$ is selected from the group consisting of F, L and W.

According to an embodiment, the peptide of the invention comprises, or consists of, a sequence selected from the group consisting of:

F-L-$X_1$-G-I-$X_2$-G-M-L-G-K-L-F (SEQ ID NO: 18),
F-L-$X_1$-G-I-V-G-$X_3$-L-G-K-L-F (SEQ ID NO: 19),
F-L-$X_1$-G-I-V-G-M-L-G-K-L-$X_4$ (SEQ ID NO: 20),
F-L-$X_1$-G-I-$X_2$-G-$X_3$-L-G-K-L-F (SEQ ID NO: 21),
F-L-$X_1$-G-I-$X_2$-G-M-L-G-K-L-$X_4$ (SEQ ID NO: 22),
F-L-$X_1$-G-I-V-G-$X_3$-L-G-K-L-$X_4$ (SEQ ID NO: 23), and
F-L-$X_1$-G-I-$X_2$-G-$X_3$-L-G-K-L-$X_4$ (SEQ ID NO: 2), wherein $X_1$, $X_2$ and $X_3$, which are the same or different, are selected from the group consisting of R, H and K, and $X_4$ is selected from the group consisting of I, L and W, preferably from the group consisting of L and W.

In a preferred embodiment, $X_1$, $X_2$ and $X_3$ represent K in SEQ ID NOs: 2 and 18 to 23. Preferably, $X_4$ represents L in SEQ ID NOs: 2, 20, 22 and 23.

According to a particular embodiment, the peptide comprises, or consists of, a sequence selected from the group consisting of:

F-L-K-G-I-K-G-M-L-G-K-L-F (SEQ ID NO: 3),
F-L-K-G-I-V-G-K-L-G-K-L-F (SEQ ID NO: 4),
F-L-K-G-I-V-G-M-L-G-K-L-L (SEQ ID NO: 5),
F-L-K-G-I-V-G-M-L-G-K-L-W (SEQ ID NO: 6),
F-L-K-G-I-V-G-M-L-G-K-L-I (SEQ ID NO: 7),
F-L-K-G-I-K-G-M-L-G-K-L-L (SEQ ID NO: 8),
F-L-K-G-I-K-G-M-L-G-K-L-W (SEQ ID NO: 9),
F-L-K-G-I-K-G-M-L-G-K-L-I (SEQ ID NO: 10),
F-L-K-G-I-V-G-K-L-G-K-L-W (SEQ ID NO: 11),
F-L-K-G-I-V-G-K-L-G-K-L-L (SEQ ID NO: 12),
F-L-K-G-I-V-G-K-L-G-K-L-I (SEQ ID NO: 13),
F-L-K-G-I-K-G-K-L-G-K-L-F (SEQ ID NO: 14),
F-L-K-G-I-K-G-K-L-G-K-L-L (SEQ ID NO: 15),
F-L-K-G-I-K-G-K-L-G-K-L-W (SEQ ID NO: 16), and
F-L-K-G-I-K-G-K-L-G-K-L-I (SEQ ID NO: 17).

Preferably, the peptide comprises, or consists of, a sequence selected from the group consisting of the sequences of SEQ ID NOs: 3 to 6, 8, 9, 11, 12 and 14 to 16. More preferably, the peptide comprises, or consists of, a sequence selected from the group consisting of the sequences of SEQ ID NOs: 3 to 6 and 8, and even more preferably from the group consisting of the sequences of SEQ ID NOs: 3, 5 and 6.

According to one embodiment, the peptide has a size comprised between 13 and 100 amino acids, preferably between 13 and 30, 35, 40, 45 or 50 amino acids. According to another embodiment, the peptide has a size comprised between 13 and 15, 20 or 25 amino acids. In a particular embodiment, the peptide has a size of 13 amino acids.

The peptide according to the invention can be a precursor of a mature antimicrobial peptide. Said precursor then undergoes post-translational modifications leading to the mature form of the AMP. It may thus comprise a translocation signal sequence and recognition and/or cleavage sites enabling it to undergo these post-translational modifications. According to a particular embodiment, the peptide is a precursor of a mature antimicrobial peptide and comprises the sequence F-L-G-T-I-N-L-S-L-C-E-Q-E-R-D-A-D-E-E-E-R-R-D-E-P-N-E-S-N-V-E-V-E-K-R-F-L-$X_1$-G-I-$X_2$-G-$X_3$-L-G-K-L-$X_4$-G-K (SEQ ID NO: 24), wherein $X_1$ is an amino acid selected from the group consisting of R, H and K, $X_2$ is an amino acid selected from the group consisting of V, R, H and K, $X_3$ is an amino acid selected from the group consisting of M, R, H and K, and $X_4$ is an amino acid selected from the group consisting of F, I, L and W, with the proviso that when $X_2$ is V, then $X_3$ is selected from the group consisting of K, R and H and/or $X_4$ is selected from the group consisting of L, I and W.

The amino acids constituting the peptide of the invention may be in the L or D configuration, preferably the L configuration.

The peptide according to the invention may have a post-translational modification and/or a chemical modification, in particular a glycosylation, an amidation, an acylation, an acetylation or a methylation.

So as to enhance the bioavailability of the peptide by improving its resistance to peptidases, protective groups may be added to the C- and/or N-terminal ends. For example, the protective group at the N-terminal end may be an acylation or an acetylation and the protective group at the C-terminal end may be an amidation or an esterification. Preferably, the peptide of the invention comprises a protective group selected from the group consisting of C-terminal amidation, N-terminal acetylation, and a combination thereof. The action of proteases may also be blocked by the use of amino acids in the D configuration, cyclization of the peptide by formation of disulfide bridges, lactam rings or bonds between the C- and N-terminal ends. The peptide of the invention may also comprise pseudo-peptide bonds replacing the "classical" CONH peptide bonds and conferring increased resistance to peptidases, such as CHOH—$CH_2$, NHCO, $CH_2$—O, $CH_2CH_2$, CO—$CH_2$, N—N, CH=CH, $CH_2$NH, and $CH_2$—S. In a preferred embodiment, the peptide according to the invention has an amidation at its C-terminal end.

The peptide according to the invention may comprise one or more amino acids which are rare amino acids, in particular hydroxyproline, hydroxylysine, allohydroxylysine, 6-N-methyllysine, N-ethylglycine, N-methylglycine, N-ethylasparagine, allo-isoleucine, N-methylisoleucine, N-methylvaline, pyroglutamine, or aminobutyric acid, or synthetic amino acids, in particular ornithine, norleucine, norvaline and cyclohexyl-alanine.

The invention also encompasses functional derivatives of a peptide according to the invention such as described above. The term "functional derivative" as employed herein refers to peptides having substantially the same amino acid sequence, substantially the same helicoid structure and substantially the same antimicrobial activity. Said functional derivatives may, for example, be retropeptides, retro-inverso peptides, peptides having conservative substitutions and peptides whose side chain of one or more amino acids is substituted by groups that do not modify the antimicrobial activity of the peptide of the invention. The term "functional derivative" also refers to a peptide according to the invention whose sequence is shortened by 1, 2, 3 or 4 amino acids at the C-terminal and/or N-terminal end, preferably by 1 or 2 amino acids at the N-terminal end.

In a particular embodiment, the term "functional derivative" refers to retro or retro-inverso peptides, preferably retro-inverso peptides, and/or peptides according to the invention comprising, or consisting of, a sequence shortened by 1 or 2 amino acids at the N-terminal end, i.e., L-$X_1$-G-I-$X_2$-G-$X_3$-L-G-K-L-$X_4$ (SEQ ID NO: 25) or $X_1$-G-I-$X_2$-G-$X_3$-L-G-K-L-$X_4$ (SEQ ID NO: 26), wherein $X_1$, $X_2$, $X_3$ and $X_4$ have the same meaning as in the above disclosed embodiments.

The present invention also relates to a peptide analogue of temporin-SHa exhibiting an antimicrobial activity and comprising, or consisting of, the sequence $X_5$-(SEQ ID NO: 27) or L-$X_5$-$X_6$-I-V-$X_7$-M-L-$X_8$-K-L-F (SEQ ID NO: 28), wherein $X_5$ is an amino acid selected from the group consisting of S, R, H and K, and $X_6$, $X_7$ and $X_8$, which are the same or different, are amino acids selected from the group consisting of G, R, H and K, and wherein, when $X_5$ represents S, at least one of the residues $X_6$, $X_7$ and $X_8$ is selected from the group consisting of R, H and K, and the functional derivatives and pharmaceutically acceptable salts of said peptide.

In a preferred embodiment, $X_5$ is an amino acid selected from the group consisting of R, H and K, and is preferably K, and $X_6$, $X_7$ and $X_8$ represent G.

In a particular embodiment, the peptide comprises, or consists of, the sequence $X_5$-$X_6$-I-V-$X_7$-M-L-$X_8$-K-L-F (SEQ ID NO: 27). Preferably, in this embodiment, $X_5$ is an amino acid selected from the group consisting of R, H and K, and is preferably K, and $X_6$, $X_7$ and $X_8$ represent G.

The invention also encompasses the pharmaceutically acceptable salts of a peptide according to the invention. Pharmaceutically acceptable salts may, for example, be salts of pharmaceutically acceptable mineral acids such as hydrochloric acid, hydrobromic acid, sulfuric acid and phosphoric acid; salts of pharmaceutically acceptable organic acids such as acetic acid, citric acid, maleic acid, malic acid, succinic acid, ascorbic acid and tartaric acid; salts of pharmaceutically acceptable mineral bases such as salts of sodium, potassium, calcium, magnesium or ammonium; or salts of organic bases which contain a salifiable nitrogen, commonly used in pharmaceutical techniques. The methods for preparing said salts are well-known to one of skill in the art.

The peptide according to the invention may be obtained by classical chemical synthesis (in solid phase or homogeneous liquid phase) or by enzymatic synthesis (Kullman et al., 1987). It may also be obtained by the method consisting of culturing a host cell, such as described hereinafter, comprising a transgene coding for the peptide and expressing said peptide, and extracting said peptide from said host cells or from the culture medium into which the peptide was secreted.

The peptide according to the invention exhibits an antimicrobial activity and a reduced cytolytic activity in comparison with temporin-SHa.

Preferably, the peptide according to the invention exhibits no or weak cytolytic activity. In particular, the peptide of the invention may have a $LC_{50}$ of more than 30 µM for erythrocytes, preferably more than 40, 50, 100, 200, 500, 600, or 800 µM. The $LC_{50}$ value may be obtained for example on rat, dog, rabbit, pig, cat or human erythrocytes, preferably on rat or human erythrocytes, more preferably on rat erythrocytes.

In addition to reduced cytotoxicity, the peptide of the invention has an antimicrobial activity that is preferably equal or superior to that of temporin-SHa against at least one bacterial, viral, fungal or parasitic strain.

The present invention also relates to a nucleic acid coding for a peptide according to the invention.

In the spirit of the invention, "nucleic acid" is understood to mean any molecule based on DNA or RNA. These may be synthetic or semi-synthetic, recombinant molecules, possibly amplified or cloned into vectors, chemically modified, comprising non-natural bases or modified nucleotides comprising for example a modified bond, a modified purine or pyrimidine base, or a modified sugar.

The nucleic acid according to the invention may be in the form of DNA and/or RNA, single-stranded or double-stranded. According to a preferred embodiment, the nucleic acid is an isolated DNA molecule, synthesized by recombinant techniques well-known to one of skill in the art.

The nucleic acid according to the invention may be deduced from the sequence of the peptide according to the invention and codon usage may be adapted according to the host cell in which the nucleic acid shall be transcribed. These steps may be carried out according to methods well-known to one of skill in the art, some of which are described in the reference manual of Sambrook et al. (2001).

The present invention further relates to an expression cassette comprising a nucleic acid according to the invention operably linked to the sequences required for its expression. In particular, the nucleic acid may be under the control of a promoter allowing its expression in a host cell. Generally, an expression cassette is constituted of or comprises a promoter allowing initiation of transcription, a nucleic acid according to the invention, and a transcription terminator. The term "expression cassette" denotes a nucleic acid construct comprising a coding region and a regulatory region, operably linked. The expression "operably linked" indicates that the elements are combined in such a way that the expression of the coding sequence (the gene of interest) and/or the targeting of the encoded peptide are under the control of the transcriptional promoter and/or signal peptide. Typically, the promoter sequence is placed upstream of the gene of interest, at a distance therefrom, which is compatible with the control of expression. Likewise, the sequence of the signal peptide is generally fused upstream of the sequence of the gene of interest, and in the same reading frame with the latter, and downstream of any promoter. Spacer sequences may be present, between the regulatory elements and the gene, as long as they do not prevent expression and/or targeting. In a preferred embodiment, said expression cassette comprises at least one "enhancer" activating sequence operably linked to the promoter.

The present invention also relates to an expression vector comprising a nucleic acid or an expression cassette according to the invention. Said expression vector may be used to transform a host cell and enables the expression of the nucleic acid of the invention in said cell.

The vector may be a DNA or an RNA, circular or not, single- or double-stranded. Advantageously it is selected from among a plasmid, a phage, a phagemid, a virus, a cosmid and an artificial chromosome.

Advantageously, the expression vector comprises regulatory elements allowing the expression of the nucleic acid according to the invention. These elements may contain for example transcriptional promoters, transcriptional activators, terminator sequences, and initiation and termination codons. The methods for selecting said elements according to the host cell in which expression is desired are well-known to one of skill in the art.

The vector may also contain elements enabling its selection in the host cell, such as an antibiotic resistance gene or a selectable gene providing complementation of the respective gene deleted from the host cell genome. Such elements are well known to one of skill in the art and extensively described in the literature.

When the host cell to be transformed is a plant cell, the expression vector is preferably a plant vector. Examples of plant vectors are described in the literature, including in particular the T-DNA plasmids of *A. tumefaciens* pBIN19 (Bevan, 1984), pPZP100 (Hajdukewicz et al., 1994), the pCAMBIA series (R. Jefferson, CAMBIA, Australia). The vectors of the invention may additionally comprise an origin of replication, a selectable marker gene and/or a plant recombination sequence.

The vectors may be constructed by the classical techniques of molecular biology, well-known to one of skill in the art.

The present invention relates to the use of a nucleic acid, an expression cassette or an expression vector according to the invention to transform or transfect a cell. The host cell may be transformed/transfected in a transient or stable manner and the nucleic acid, cassette or vector may be contained in the cell in the form of an episome or in chromosomal form.

The present invention relates to a host cell comprising a nucleic acid, a cassette or an expression vector according to the invention.

According to one embodiment, the host cell is a microorganism, preferably a bacterium or a yeast.

According to another embodiment, the host cell is an animal cell, for example a mammalian cell such as COS or CHO cells (U.S. Pat. No. 4,889,803; U.S. Pat. No. 5,047,335). In a particular embodiment, the cell is non-human and non-embryonic.

According to yet another embodiment, the host cell is a plant cell. The term "plant cell" as employed herein refers to any cell coming from a plant and which may constitute undifferentiated tissues such as calluses and differentiated tissues such as embryos, plant parts, plants or seeds.

The present invention also relates to a method for producing an antimicrobial peptide according to the invention, comprising transforming or transfecting a cell with a nucleic acid, an expression cassette or an expression vector according to the invention; culturing the transfected/transformed cell; and recovering the peptide produced by said cell. Methods for producing recombinant peptides are well-known to one of skill in the art. For example, one may cite the specific methods described in WO 01/70968 for production in an immortalized human cell line, WO 2005/123928 for production in a plant and US 2005/229261 for production in the milk of a transgenic animal.

The present invention also relates to a method for producing an antimicrobial peptide according to the invention, comprising inserting a nucleic acid, a cassette or an expression vector according to the invention in an in vitro expression system, also called acellular, and recovering the peptide produced by said system. Many in vitro or acellular expression systems are commercially available and the use of said systems is well-known to one of skill in the art.

The present invention additionally relates to a peptide according to the invention as a medicament, in particular as a medicament for treating a microbial infection, namely an infection due to a bacterium, virus, fungus or parasite. It also relates to a nucleic acid, cassette or vector according to the invention as a medicament. The medicament may be intended for pharmaceutical or veterinary use.

The microbial infection may be an infection due to a parasite, in particular a parasite from the genus *Leishmania* or *Trypanosoma*.

In an embodiment, the microbial infection is an infection due to a parasite from the genus *Leishmania*. The infection may be a cutaneous leishmaniosis, a mucocutaneous leishmaniosis or a visceral leishmaniosis. The parasite may be selected from the group consisting of *Leishmania aethiopica, Leishmania amazonensis, Leishmania arabica, Leishmania aristedes, Leishmania braziliensis, Leishmania infantum, Leishmania colombiensis, Leishmania deanei, Leishmania donovani, Leishmania enriettii, Leishmania equatorensis, Leishmania forattinii, Leishmania garnhami, Leishmania gerbili, Leishmania guyanensis, Leishmania herreri, Leishmania hertigi, Leishmania killicki, Leishmania lainsoni, Leishmania major, Leishmania mexicana, Leishmania naiffi, Leishmania panamensis, Leishmania peruviana, Leishmania pifanoi, Leishmania shawi, Leishmania turanica, Leishmania tropica* and *Leishmania venezuelensis*. Preferably, the parasite is selected from the group consisting of *Leishmania infantum, Leishmania donovani, Leishmania mexicana, Leishmania amazonensis, Leishmania major, Leishmania tropica, Leishmania braziliensis, Leishmania guyanensis, Leishmania panamensis* and *Leishmania peruviana*. In a particularly preferred manner, the parasite is selected from the group consisting of *Leishmania infantum, Leishmania donovani, Leishmania major, Leishmania tropica, Leishmania amazonensis, Leishmania killicki* and *Leishmania braziliensis*. In a most particularly preferred manner, the infection is an infection by the parasite *Leishmania infantum*.

In another embodiment, the microbial infection is an infection due to a parasite from the genus *Trypanosoma*. The parasite may be selected from the group consisting of *Trypanosoma avium, Trypanosoma brucei, Trypanosoma cruzi, Trypanosoma congolense, Trypanosoma equinum, Trypanosoma equiperdum, Trypanosoma evansi, Trypanosoma lewisi, Trypanosoma melophagium, Trypanosoma percae, Trypanosoma rangeli, Trypanosoma rotatorium, Trypanosoma simiae, Trypanosoma suis, Trypanosoma theileri, Trypanosoma triglae* and *Trypanosoma vivax*. Preferably, the parasite is selected from the group consisting of *Trypanosoma brucei, Trypanosoma cruzi* and *Trypanosoma congolense*.

The microbial infection may be due to Gram-negative bacteria. In particular, the Gram-negative bacteria may be selected from the group consisting of *Escherichia coli* and bacteria from the genera *Pseudomonas, Salmonella, Acinetobacter* or *Klebsiella*. Preferably, Gram-negative bacteria are selected from the group consisting of *Escherichia coli, Pseudomonas aeruginosa, Salmonella enterica, Acinetobacter baumannii* and *Klebsiella pneumoniae*.

The microbial infection may be due to Gram-positive bacteria. In particular, the Gram-positive bacteria may be selected from the group consisting of bacteria from the genera *Staphylococcus, Streptococcus, Listeria* or *Enterococcus*. Preferably, Gram-positive bacteria are selected from the group consisting of *Staphylococcus aureus, Streptococcus pyogenes, Listeria ivanovii* and *Enterococcus faecalis*.

The microbial infection may also be due to a fungus. In particular, the fungus may be from the genera *Candida* or *Aspergillus*. For example, the fungus may be selected from the group consisting of *Candida albicans* and *Candida parapsilosis*.

In a particular embodiment, the peptide of the invention is used to treat a bacterial infection involving biofilm formation such as cystic fibrosis, endocarditits, and cystitis, infections caused by indwelling medical devices, dental plaque formation or periodontitis.

The present invention relates to a peptide according to the invention as an antimicrobial agent. The present invention also relates to a nucleic acid, cassette or vector according to the invention as an antimicrobial agent.

The present invention relates to a peptide according to the invention as an immune system stimulating agent, particularly during a microbial infection. The invention also relates to a nucleic acid, cassette or vector according to the invention as an immune system stimulating agent. According to a particular embodiment of the invention, the peptide according to the invention has chemotactic properties. The peptide induces the recruitment of immune cells to the site of the infection and increases the effectiveness of the immune response to infections.

The present invention also relates to a pharmaceutical composition comprising, or consisting essentially of, at least one peptide according to the invention and a pharmaceutically acceptable support and/or excipient. In particular, the pharmaceutical composition may comprise, or consist of, 1, 2, 3, 4 or 5 peptides according to the invention and a pharmaceutically acceptable support and/or excipient.

The present invention also relates to a pharmaceutical composition comprising, or consisting essentially of, at least one nucleic acid, cassette or vector according to the invention and a pharmaceutically acceptable support and/or excipient.

The pharmaceutically acceptable excipients and supports that can be used in the composition according to the invention are well-known to one of skill in the art (Remington's Pharmaceutical Sciences, $18^{th}$ edition, A. R. Gennaro, Ed., Mack Publishing Company (1990); Pharmaceutical Formulation Development of Peptides and Proteins, S. Frokjaer and L. Hovgaard, Eds., Taylor & Francis (2000); and Handbook of Pharmaceutical Excipients, $3^{rd}$ edition, A. Kibbe, Ed., Pharmaceutical Press (2000)) and comprise in particular physiological saline solutions and phosphate buffers.

The pharmaceutical composition according to the invention may be suitable for local or systemic administration, in particular for oral, sublingual, cutaneous, subcutaneous, intramuscular, intravenous, intraperitoneal, topical, intratracheal, intranasal, transdermal, rectal, intraocular or intraauricular administration. Preferably, the pharmaceutical composition according to the invention is suitable for cutaneous, oral, topical, intramuscular, intravenous, transdermal or subcutaneous administration. According to a particular embodiment, the pharmaceutical composition according to the invention is suitable for topical administration. The pharmaceutical composition according to the invention may be in the form of tablets, capsules, soft capsules, granulates, suspensions, emulsions, solutions, gels, pastes, ointments, creams, plasters, potions, suppositories, enemas, injectables, implants, patches, sprays or aerosols.

According to one embodiment, the composition according to the invention comprises from 1 to 2000 mg of peptide according to the invention. Preferably, the composition according to the invention comprises from 50 to 100, 150, 200, 250, 500, 750, 1000 or 1500 mg of peptide according to the invention.

The composition according to the invention may further comprise additional active substances, such as other antimicrobial agents, in particular antimicrobial peptides or antibiotics. The composition may also additionally comprise substances that can potentiate the activity of the peptide according to the invention.

The present invention relates to the use of a peptide according to the invention for preparing a medicament for treating a microbial infection. The invention also relates to the use of a nucleic acid, cassette or vector according to the invention for preparing a medicament for treating a microbial infection.

The present invention relates to a peptide according to the invention for use in the treatment of a microbial infection. The present invention also relates to a nucleic acid, cassette or vector according to the invention for use in the treatment of a microbial infection.

The treatment may be curative or preventive.

The subject to be treated is an animal, preferably a mammal. According to a particular embodiment, the subject to be treated is a human.

The present invention also relates to a method for treating a microbial infection comprising administering a therapeutically effective dose of a peptide, nucleic acid, cassette or vector according to the invention.

The term "therapeutically effective dose" as employed herein refers to the amount of peptide, nucleic acid, cassette or vector according to the invention required in order to observe an antimicrobial activity on the bacterium, virus, fungus or parasite responsible for the infection. The amount of peptide, nucleic acid, cassette or vector according to the invention to be administered and the duration of the treatment are determined by a person skilled in the art according to the physiological condition of the subject to be treated, the pathogenic agent and the antimicrobial activity of the peptide towards said pathogenic agent.

In a particular embodiment, the microbial infection to be treated is leishmaniosis.

In another particular embodiment, the microbial infection to be treated is a bacterial infection involving biofilm formation such as cystic fibrosis, endocarditits, and cystitis, infections caused by indwelling medical devices, dental plaque formation or periodontitis.

An effective dose of the peptide of the invention may comprise, but is not limited to, between approximately 1 and 40 mg/kg of body weight. The frequency of administration may be for example every 4 to 24 hours, preferably every 8 to 12 hours. The duration of treatment may be for example from 1 to 30 days, preferably from 10 to 20 days, and most preferably from 5 to 10 days.

The present invention also relates to the use of the peptide according to the invention as a preservative, disinfectant or pesticide.

Food products may be treated with a peptide according to the invention in order to eliminate or prevent the risk of infection by microorganisms and thereby improve their conservation. In this case the peptide is used as a preservative.

The peptide according to the invention may be used as a pesticide. In this case the peptide is used to prevent or treat infections of plants by phytopathogens.

The peptide according to the invention may also be used as a disinfectant. The term "disinfectant" refers to an antimicrobial activity of the peptide on a surface (for example, walls, doors, medical equipment), a liquid (for example, water) or a gas (for example, an anesthetic gas).

Biofilms are responsible for approximately 60% of nosocomial infections. They are essentially due to microbial colonization of implanted biomaterials. Eradication of a bacterial biofilm is a major clinical problem considering that antibiotics normally active on bacteria in a planktonic state often turn out to be much less effective against structures organized into a biofilm. The effect of the antimicrobial peptides on this type of biofilm has been demonstrated in previous studies carried out with temporin-A (Cirioni et al., 2003).

According to one embodiment, the peptide according to the invention is used for elimination of bacterial biofilms. According to a preferred embodiment, the peptide according to the invention is used in particular for disinfecting surgical or prosthetic equipment.

The present invention also relates to a medical device or implant comprising a body having at least one surface coated with or including a peptide according to the invention. The present invention also relates to a method for preparing a medical device or implant comprising applying a coating of a peptide according to the invention, or placing in contact with at least one surface of the device or implant.

This type of medical device or implant and the uses and methods of preparation thereof are described for example in patent application WO 2005/006938.

The surface coated with or including a peptide according to the invention may be composed of thermoplastic or polymeric materials such as polyethylene, Dacron, nylon, polyesters, polytetrafluoroethylene, polyurethane, latex, silicone elastomers and the like, or metallic materials such as gold. In a particular embodiment, the peptide of the invention is covalently attached to a functionalized surface, preferably a metallic surface, via its N-terminal or C-terminal end. Optionally, the peptide may be attached to the surface through a spacer arm.

Preferably, the surface may be coated with a peptide at a density of 0.4 to 300 mg/cm$^2$.

Alternatively, the device or implant, in particular a bone and joint prosthetic device, may be coated with a cement mixture comprising a peptide according to the invention.

The peptide may be combined with another active molecule, preferably an antibiotic.

The devices or implants may be, for example, intravascular, peritoneal, pleural or urological catheters; heart valves; cardiac pacemakers; vascular shunts; coronary shunts; dental implants; or orthopaedic or intraocular prostheses.

The present invention relates to a food composition comprising at least one peptide according to the invention.

The present invention also relates to an agrochemical composition comprising at least one peptide according to the invention.

The present invention relates to a transgenic plant comprising a nucleic acid, a cassette or an expression vector according to the invention, and able to express or expressing a peptide according to the invention.

Introduction of nucleic acids, cassettes or expression vectors of the invention in a cell or a plant tissue, including a seed or plant, may be carried out by any method known to one of skill in the art. Plant transgenesis methods are well-known in the field, and comprise for example the use of the bacterium *Agrobacterium tumefaciens* (Hooykaa and Schilperoort, 1992), electroporation, conjugative transfer, biolistic techniques (Russel et al., 1992) or microinjection into plant embryos or protoplasts. Other plant transgenesis techniques are well-known, and other protocols implementing the above techniques are described in the prior art (Siemens and Schieder, 1996) and may be applied to the present invention. The transgenic plant according to the invention may be obtained in particular according to the method described in patent application WO 00/055337.

The transgenic plant may belong to any plant species. It may be monocotyledonous or dicotyledonous. More particularly, the transgenic plant of the invention is a cultured plant intended or not intended for animal or human food or on which the sandfly, the insect vector of leishmaniosis, alights to feed, such as maize, wheat, rapeseed, soy, alfalfa, flax, rice, sugar cane, beet, tobacco, cotton, sunflower, tomato, cabbage, carrot, potato, or fruit trees such as the lemon tree, apple tree, apricot tree, peach tree and hazel tree, or plants identified to date as sugar meal sources for sandflies such as *Ricinus communis, Capparis spinosa, Solanum jasminoides, Solanum luteum* or *Bougainvillea glabra.*

According to one embodiment, the expression of the peptide according to the invention allows the transgenic plant to have increased resistance to pathogens, and more particularly to phytopathogens. The use of such transgenic plant makes it possible to considerably reduce the spraying or application of pesticides on the crops, and thereby to minimize the harmful environmental effects of these products.

According to another embodiment, the transgenic plant expresses a peptide according to the invention, which is administered to an animal including sandflies or a human by ingestion of said plant or its juices. In this case, the peptide does not necessarily have an effect on the phytopathogens but displays antimicrobial activity against one or more pathogens of the animal including the *leishmania* parasites present in the gut of the sandfly vectors of human and animal leishmaniosis or the human to which it is administered. The transgenic plants on which the sandflies take their sugar meal directly deliver into the gut of the insect vector an antimicrobial peptide of the invention which kills the parasite eventually present in the insect vector directly or by blocking its development by killing the bacteria of the intestinal flora of the insect vector, required for parasite differentiation or multiplication. Transgenic plants in fact constitute an effective means of indirect control of transmission of leishmaniosis.

The present invention relates to an antibody specific to the peptide according to the invention. The term "antibody" as employed herein refers in particular to polyclonal or monoclonal antibodies, fragments thereof (for example, the fragments F(ab)'2 or F(ab)), single chain antibodies or minibodies or any polypeptide comprising a domain of the initial antibody recognizing the peptide of the invention, particularly CDRs (complementarity-determining regions). For example these are chimeric, humanized or human antibodies. Monoclonal antibodies may be prepared from hybridomas according to methods well-known to one of skill in the art. The different methods for preparing antibodies are well-known to one of skill in the art.

The present invention also relates to the use of an antibody according to the invention for detecting a peptide according to the invention. It further relates to the use of an antibody according to the invention for making quantitative measurements of a peptide according to the invention, in particular for immunological assays. Said measurements can in particular allow a determination of the expression of the peptide of the invention in a host cell or a transgenic plant according to the invention.

All the references cited in this description are incorporated by reference in the present application. Others features and advantages of the invention will become clearer in the following examples, which are given for purposes of illustration and not by way of limitation.

EXAMPLES

Materials and Methods
Solid Phase Peptide Synthesis

Solid phase peptide synthesis was carried out with the aid of an automated peptide synthesizer (Applied Biosystems 433A) according to the protocol described by Vanhoye et al. (2004), and by using Fmoc-protected amino acids (Novabiochem, Switzerland) and Rink amide MBHA resin (Senn Chemicals, Switzerland).

The lyophilized crude peptides were purified by RP-HPLC on a Phenomenex Luna® C18(2) semi-preparative column (10 µm, 250×10 mm) eluted at a flow rate of 5 mL/min by a 0-70% linear gradient of acetonitrile (0.07% trifluoroacetate) in 0.1% trifluoroacetate/water (1% acetonitrile/min). The homogeneity and identity of the synthetic peptides were assessed by matrix-assisted laser desorption/ionization-time of flight (MALDI-TOF) mass spectrometry (Voyager DE-PRO, Applied Biosystems) and RP-HPLC on a C18 analytical column (Modulo-Cart QS Uptisphere® 5ODB, 5 µm, 250×4.6 mm, Interchim) using the above conditions with a flow rate of 0.75 mL/min.

Tests of Antibacterial Activity

The following strains were used for the antibacterial activity tests: *Escherichia coli* (ATCC 25922 and ML-35p), *Staphylococcus aureus* (ATCC 25923 and ST1065), *Enterococcus faecalis* (ATCC 29212), *Pseudomonas aeruginosa* (ATCC 27853), *Streptococcus pyogenes* (ATCC 19615), *Listeria ivanovii, Salmonella enterica* (serotype *Enteritidis*), *Acinetobacter baumannii* (ATCC 19606) and *Klebsiella pneumoniae* (ATCC 13883). Two antibiotic-resistant strains were also used (*S. aureus* ATCC 43300 and ATCC BAA-44).

For each strain, a standard inoculum of approximately $10^6$ bacteria/mL (exponential growth phase) was prepared. To this end, a colony isolated on LB agar previously inoculated with one of the strains was cultured in 4 mL of LB broth medium, except for *S. pyogenes* and *L. ivanovii*, which were grown in BHI (Brain Heart Infusion) from a colony isolated on BHI agar. Liquid cultures were then incubated for 2 to 3 hrs at 37° C. with shaking for the bacteria to reach exponential growth phase. After centrifugation, most of the bacterial suspensions were diluted in Mueller-Hinton (MH) broth medium to an $OD_{630nm}$ of 0.01, which corresponds to a concentration of approximately $10^6$ cfu/mL (cfu: colony forming unit). A different medium was used for *E. faecalis* (LB) and for *S. pyogenes* and *L. ivanovii* (BHI).

The minimum inhibitory concentration (MIC) of each peptide was determined by a test of growth inhibition in broth medium. MIC is defined as the lowest concentration of peptide able to inhibit the growth of the bacterial strain tested after 18 hrs of incubation at 37° C. The test was performed in a sterile 96-well microtiter plate. A series of increasing concentrations of peptide (2 to 400 µM) was first prepared in sterile MilliQ water. 50 µL of each peptide concentration were mixed into the well with 50 µL of bacterial suspension ($10^6$ cfu/mL). The microtiter plate was then incubated for 18 hrs at 37° C. with shaking. Bacterial growth was determined by measuring OD at 630 nm (turbidity) on a plate reader. Tests were carried out in triplicate for each peptide concentration and at least three independent experiments were performed to determine the MIC value.

The growth inhibition negative control was obtained by replacing the solution containing the peptide with 50 µL of sterile MilliQ water. The positive control allowing the complete inhibition of bacterial growth was obtained by replacing the solution containing the peptide with 50 µL of 0.7% formaldehyde.

Tests of Antifungal Activity

Three yeast strains were used: *Saccharomyces cerevisiae, Candida albicans* (ATCC 90028), *Candida parapsilosis* (ATCC 22019). These strains were first grown on YPD agar for a minimum of 48 hrs. Yeast suspensions were then prepared, exactly as for bacteria, and adjusted to $10^6$ cfu/mL in YPD broth medium.

The antifungal activity test corresponds to the growth inhibition test in broth medium used for the bacteria (see above) in which MH medium was replaced by YPD medium. Fungal strains were incubated at 30° C.

Tests of Anti-Leishmanial Activity

Leishmanicidal activity of peptides was evaluated on the promastigote form of *Leishmania infantum* (strain MHOM/MA/67/ITMAP-263), responsible for visceral leishmaniosis.

Promastigotes were maintained at 26° C. by one or two weekly passages, depending on the number of parasites in the inoculum, in SDM 79 medium supplemented with 10 to 20% decomplemented fetal calf serum and 5 mg/mL porcine hemin and in the presence of 100 U/mL penicillin and 100 µg/mL streptomycin (Brun et al., 1979). Starting from an inoculum of $10^5$ cells/mL in logarithmic growth phase, the promastigotes reached a cell density of 1 to $2 \times 10^8$ parasites/mL in stationary phase after 5 days of culture in 25 cm² culture flasks. Cell densities were determined by flow cytometry in the presence of propidium iodide on a FAC Scan cytometer (Excalibur, Becton Dickinson, Ivry, France).

The tests of anti-leishmanial activity were carried out with a parasite line expressing the luciferase. This parasite line was obtained by transforming a *Leishmania infantum* strain with the vector pGM-αNEO-αLUC containing the reporter gene LUC that codes for the firefly luciferase, and the neomycin resistance gene (NEO) such as described in Roy et al. (2000).

Tests of anti-leishmanial activity on promastigotes expressing the luciferase

80 µL of a promastigote suspension ($10^5$ parasites/well) were aliquoted into each well of a microtiter plate together with 20 µL of peptide solution (50 to 3.125 µM final concentration). For the negative control the peptide solution was replaced by 20 µL of SDM79 medium. The positive control was carried out with 20 µL of the solution with the highest peptide concentration. Experiments were done in triplicate for each peptide concentration.

After 72 hrs of incubation at 26° C., 50 µL of Steady-Glo lysis buffer (Promega) were added to each well. After a 5-min incubation at room temperature, cell lysis was checked under a microscope. Emitted luminescence was measured with a luminescence plate reader (Victor, PerkinElmer). It is proportional to the number of viable parasites in the medium. The percentage growth was calculated according to the following formula:

% growth=[($L$ mean–$bgd$)$_{peptide}$×100]/($L$ mean– $bgd$)$_{negative\ control}$ where L mean: mean luminescence and bgd: background corresponding to the luminescence emitted by the culture medium. The concentration inhibiting promastigote growth by 50% ($IC_{50}$) was determined.

Cytotoxicity Tests on Rat Erythrocytes, Human Monocytes, Macrophages, Hepatocellular Liver Carcinoma Cells and Fibroblasts The cytotoxic activity of the antimicrobial peptides was ascertained on rat erythrocytes, the human leukemia monocyte cell line THP-1, THP-1 monocyte-derived macrophages, HepG2 human hepatoma-derived cells (human hepatocellular liver carcinoma cell line) and human fibroblasts. Macrophages are the host cells for *Leishmania*.

Hemolytic Test

The hemolytic activity of the antimicrobial peptides was assessed using rat erythrocytes. Red blood cell hemolysis is manifested by the release into the reaction medium of hemoglobin, the concentration of which is determined spectrophotometrically at 450 nm.

Red blood cells were separated from plasma and white blood cells by centrifugation of blood (900×g, 10 min). The pellet containing red blood cells was washed three times with PBS buffer, pH 7.4. After counting on a Malassez cell, a stock solution of $4 \times 10^8$ red blood cells/mL was prepared in the same buffer. A series of concentrations of the peptides to be tested was prepared (2 to 400 µM).

The test was carried out as follows: 50 µL of the different peptide concentrations were added to 50 µL of the red blood cell suspension. After 1 hr of incubation at 37° C. followed by centrifugation (12,000×g, 15 sec), absorbance of the supernatant was measured at 450 nm. The negative control for this test (0% hemolysis) contained 50 of PBS buffer in place of the peptide solution. The positive control (100% hemolysis) contained 50 µL of 0.1% Triton X-100 in place of the peptide solution.

The $LC_{50}$ value obtained is the mean of three experiments carried out in triplicate and corresponds to the peptide concentration inducing hemolysis of 50% of the cells.

Cytotoxicity Test on Monocytes

Cells were cultured in RPMI medium (10% FCS, 1/100 Glutamax® (Invitrogen) and 100 U/mL penicillin, 100 µg/mL streptomycin) until reaching exponential growth phase. After counting in a Thoma counting chamber, cell density was adjusted to $6.25 \times 10^5$ cells/mL in RPMI 1640 medium. Five-fold concentrated solutions of antimicrobial peptides were prepared in this RPMI medium (250 to 15.6 µM).

Cells were aliquoted at 80 µL of cell suspension per well (corresponding to $5 \times 10^4$ monocytes/well or $5 \times 10^5$ cells/mL final) and mixed with 20 µL of peptide solution (50 to 3.125 µM final concentration). Negative and positive controls were carried out according to the same protocol as for the tests of anti-leishmanial activity. Experiments were done in triplicate for each peptide concentration. Cells were incubated at 37° C., in a 5% $CO_2$ atmosphere for 72 hrs.

After 72 hrs, the number of viable cells was estimated indirectly by the MTT test (Mosmann, 1983). MTT (or 3-(4,5-dimethylthiazol-2-yl)-2,5-diphenyl-tetrazolium bromide), which is yellow in color, is reduced to formazan, which is blue in color, by the action of succinate-tetrazolium reductase, which is present in the mitochondrial respiratory chain of metabolically active cells. Blue formazan can be detected spectrophotometrically at 570 nm.

A 10 mg/mL MTT solution in PBS buffer (pH 7.4), filtered on a 0.22 µm filter, was aliquoted at 10 µL per well. Plates were then incubated for 4 hrs at 37° C. The enzymatic reaction was stopped by adding 100 µl of a 50% isopropanol/10% SDS mixture and the plates were then incubated at room temperature for 30 min with shaking. The OD at 570 nm of each well was then measured (Victor plate reader, PerkinElmer). The percentage of growth was calculated as follows:

% growth=[($OD$ mean–$bgd$)$_{peptide}$×100]/($OD$ mean– $bgd$)$_{negative\ control}$ where bgd is the background corresponding to the absorbance by the culture medium. The negative control (100% growth) did not contain peptide.

$IC_{50}$ was then determined from the percentage of growth.

Cytotoxicity Test on THP-1 Human Monocytes-Derived Macrophages

The viability of macrophages was ascertained using a trypan blue-based microassay. THP-1 cells from a culture suspension in mid-log phase of growth were plated at a density of $5\times10^5$ cells/mL in 96-well plates (100 µL/well, i.e., $5\times10^4$ cells/well) and differentiated as described above. After incubation for 72 hrs at 37° C. with 5% $CO_2$, in the presence of peptide (60 µM to 7.5 µM, final concentrations), adherent macrophages were washed once with prewarmed RPMI 1640 medium and stained for 5 min, with 100 µL of trypan blue 2-fold diluted in RPMI 1640 medium. Wells were then washed twice with 100 µL of RPMI 1640 medium. Living white cells were microscopically counted in three focuses per well using a reticulated ocular.

The viability index (VI) was calculated for each peptide concentration using the following formula:

$$VI = [N\ \text{mean}_{peptide} \times 100]/N\ \text{mean}_{negative\ control}.$$

where N mean is the mean number of viable parasites. The negative control (100% growth) contained 20 µL of RPMI medium in place of the peptide solution.

The $LC_{50}$ value, which corresponds to the peptide concentration inducing lysis of 50% of the cells, was determined from the viability indexes. Tests were carried out in sextuplicate for each peptide concentration and at least two independent experiments were performed to determine the $LC_{50}$ value.

Cytotoxicity Test on HepG2 Human Hepatoma-Derived Cells

HepG2 human hepatoma-derived cells were seeded onto a 96-well plate at a density of $5\times10^5$ cells/mL (100 µL/well, i.e., $5\times10^4$ cells/well) in MEM medium supplemented with 10% decomplemented fetal calf serum, 1/100 Glutamax® (Invitrogen), 100 IU of penicillin/mL and 100 µg of streptomycin/mL, and allowed to grow and adhere for 72 hrs at 37° C. and 5% $CO_2$. Serial dilutions of peptide were added in 100 µL of supplemented MEM medium (100 µM to 600 µM). After incubation for 72 hrs, cell viability was assessed using the MTT-based microassay as described earlier for human monocytes THP-1.

The $LC_{50}$ was then determined from the calculated percentages of growth for each peptide concentration. Tests were carried out in triplicate for each peptide concentration and at least three independent experiments were performed to determine the $LC_{50}$ value.

Cytotoxicity Test on Fibroblasts

Human foreskin fibroblasts were cultivated in Dulbecco's modified Eagle medium (DMEM, Invitrogen) supplemented with 10% fetal bovine serum (FBS, Invitrogen), 4 mM glutamine, 500 U/ml penicillin, and 250 µg/ml streptomycin at 37° C. in 5% $CO_2$. $10^4$ cells per well (96-well plate) were seeded. After 24 hrs, serial dilutions of peptide were added and the tetrazolium compound (3-(4,5-dimethylthiazol-2-yl)-5-(3-carboxymethoxyphenyl)-2-(4-sulfophenyl)-2H-tetrazolium) was added directly to culture wells after a 72 hr proliferation phase. The bioreduced colored formazan produced by viable cells was quantified with a 96-well plate reader (absorbance, 490 nm). The $LC_{50}$ was determined by nonlinear regression analysis.

Results

On the basis of their physicochemical properties, a series of deleted or substituted analogues of temporin-SHa were designed to obtain potent antimicrobial activity and reduced cytotoxicity (FIG. 2). The antimicrobial activity of these analogues was evaluated on different Gram-positive, Gram-negative and antibiotic-resistant bacterial reference strains and on fungal strains.

*L. infantum*, the main causal agent of human visceral leishmaniasis in the Mediterranean basin and Latin America, was selected as the reference *Leishmania* species (strain MHOM/MA/67/ITMAP-263) to evaluate the anti-leishmanial activity of analogues of temporin-SHa of the invention.

Activity tests were performed on the promastigote form, which is the development stage present in the insect vector, the sandfly. Evaluation of the metabolic activity of *Leishmania infantum* expressing the luciferase gene is based on oxidation of luciferin by luciferase in the presence of ATP. This process leads to the emission of photons, of which the signal intensity is proportional to the number of viable parasites and therefore to the percentage of growth.

Antimicrobial and antiparasitic activities must be determined comparatively with the toxicity of peptides on host cells. The cytotoxicity of these peptides was therefore evaluated on rat erythrocytes, the HepG2 (human hepatocellular liver carcinoma) cell line, human fibroblasts, the THP-1 human leukemia monocyte cell line and THP-1 monocyte-derived macrophages. Erythrocytes, the HepG2 (human hepatocellular liver carcinoma) cell line and human fibroblasts are the reference cell types commonly used in pharmacology to study the cytotoxicity of drugs. Macrophages are the natural host cells of *Leishmania* in mammals.

Minimum inhibitory concentrations (MIC), inhibitory concentrations 50 ($IC_{50}$) and lethal concentrations 50 ($LC_{50}$) are shown in FIGS. 4 and 5.

Antibacterial and Antifungal Activities

The results indicate that $[K^3]$temporin-SHa is a potent broad-spectrum antimicrobial agent acting with the same efficiency (MIC=3-6 µM) against Gram-positive (including antibiotic-resistant *S. aureus* strains) and Gram-negative bacterial strains of clinical interest, as well as yeasts (FIG. 4). Internal deletions (deletion of residues $V^6$ and $M^8$) and C-terminal truncation of two residues in the sequence of $[K^3]$temporin-SHa lead to inactive peptides (data not shown), except for $[K^3]$temporin-SHa(3-13), which conserve an activity against Gram-positive and Gram-negative bacteria (FIG. 4). Interestingly, this N-terminal truncated analogue is 2-fold more active than temporin-SHa against yeasts (*C. albicans* and *parapsilosis*) and *P. aeruginosa* (a Gram-negative strain resistant to the majority of temporins) and has lost its hemolytic activity ($LC_{50}$=618 µM). The absence of activity for the C-terminal truncated analogue $[K^3]$temporin-SHa(1-11), that have physicochemical properties similar to $[K^3]$temporin-SHa(3-13), reveals that the C-terminal hydrophobic tail of temporin-SHa is essential for antimicrobial activity. The fact that the N-ter and C-ter truncated analogue $[K^3]$temporin-SHa(3-11) is also inactive confirms the importance of the C-terminal.

The results of FIG. 5 reveal that $[K^3,L^{13}]$ and $[K^3,W^{13}]$ temporin-SHa, two analogues with physicochemical properties identical to $[K^3]$temporin-SHa, display potent activity with an antimicrobial activity similar to $[K^3]$temporin-SHa but, interestingly, with a lower hemolytic activity (2-fold lower, notably, for $[K^3,L^{13}]$temporin-SHa). The equally active analogues $[K^3,K^6]$, $[K^3,K^8]$, and $[K^3, K^8,L^{13}]$temporin-SHa have several features that make them very attractive. Indeed, despite their lower efficiency compared to $[K^3]$temporin-SHa, these analogues conserve a good activity against most of the strains tested (bacteria and yeasts) and are not hemolytic ($LC_{50}$>500 They are also more active than temporin-SHa against *P. aeruginosa* (4-fold) and *Candida* (2-fold).

Antiparasitic Activity

All substituted analogues of Temporin-SHa display an unequal diminution of their activity on *L. infantum* promastigotes, which approaches the cytotoxicity level of monocytes for the analogues, $[K^3,K^6]$, $[K^3,K^8]$ and $[K^3, K^6, L^{13}]$temporin-SHa (FIG. 5). As for bacteria, the anti-leishmanial activity of the analogues $[K^3,L^{13}]$ and $[K^3,W^{13}]$ temporin-SHa is little altered.

CONCLUSION

Temporin-SHa and their analogues display a broad spectrum of activity since they are able to prevent the growth of Gram-positive and Gram-negative bacteria, which are prokaryotes, as well as yeasts, which are eukaryotes.

[K$^3$]temporin-SHa, with a Lys residue instead of a Ser residue in the polar face of the α-helix, represents a more potent antimicrobial analogue compared to temporin-SHa.

The deletion of two residues (F and L) in the N-terminal region of [K$^3$]temporin-SHa yielded the analogue [K$^3$]temporin-SHa(3-13), which is devoid of hemolytic activity and has a better activity than temporin-SHa (2 fold) against *C. albicans, C. parapsilosis* and *P. aeruginosa*.

Interestingly, the analogues [K$^3$,L$^{13}$] and [K$^3$,W$^{13}$]temporin-SHa are as potent as [K$^3$]temporin-SHa and lesser haemolytic. Moreover, they display a moderate leishmanicidal activity against *L. infantum* promastigotes (similar to temporin-SHa) with reduced cytotoxicity against the host cell (macrophage) for [K$^3$,L$^{13}$]temporin-SHa.

Finally, it was shown that an additional insertion of a Lys residue in position 6 or 8 in the sequence of [K$^3$]temporin-SHa (analogues [K$^3$,K$^6$], [K$^3$,K$^8$] and [K$^3$, K$^8$,L$^{13}$]temporin-SHa) leads to good antimicrobial agents against bacteria and yeasts with no hemolytic activity.

BIBLIOGRAPHIC REFERENCES

Abbassi F, Oury B, Blasco T, Sereno D, Bolbach G, Nicolas P, Hani K, Amiche M, Ladram A (2008) Isolation, characterization and molecular cloning of new temporins from the skin of the North African ranid *Pelophylax saharica*. Peptides 29: 1526-33.

Abbassi F, Raja Z, Oury B, Gazanion E, Piesse C, Sereno D, Nicolas P, Foulon T, Ladram A (2013) Antibacterial and leishmanicidal activities of temporin-SHd, a 17-residue long membrane-damaging peptide. Biochimie 95: 388-99.

Abbassi F, Lequin O, Piesse C, Goasdoué N, Foulon T, Nicolas P, Ladram A (2010) Temporin-SHf, a new type of phe-rich and hydrophobic ultrashort antimicrobial peptide. J Biol Chem 285: 16880-92.

Brun R, Schönenberger M (1979) Cultivation and in vitro cloning or procyclic culture forms of *Trypanosoma brucei* in a semi-defined medium. Acta Trop. 36: 289-92.

Bevan M (1984) Binary *Agrobacterium* vectors for plant transformation. Nucleic Acids Res. 12: 8711-21.

Camargo, E. P. 1964. Growth and differentiation in *Trypanosoma cruzi*. I. Origin of metacyclic trypanosomes in liquid media. *Rev. Instil. Med. Trop. Sao Paulo* 6: 93-100.

Chinchar V G, Bryan L, Silphadaung U, Noga E, Wade D, Rollins-Smith L (2004) Inactivation of viruses infecting ectothermic animals by amphibian and piscine antimicrobial peptides. Virology 323: 268-75.

Cirioni O, Giacometti A, Ghiselli R, Dell'Acqua G, Gov Y, Kamysz W, Lukasiak J, Mocchegiani F, Orlando F, D'Amato G, Balaban N, Saba V, Scalise G (2003) Prophylactic efficacy of topical temporin A and RNAIII inhibiting peptide in a subcutaneous rat Pouch model of graft infection attributable to Staphylococci with intermediate resistance to glycopeptides. Circulation 108: 767-71.

Conlon J M (2008) Reflections on a systematic nomenclature for antimicrobial peptides from the skins of frogs of the family Ranidae. Peptides 29: 1815-9.

Conlon J M, Kolodziejek J, Nowotny N (2009) Antimicrobial peptides from the skins of North American frogs. Biochim. Biophys. Acta, 1788: 1556-63.

Cunningham, I. 1977. New culture medium for maintenance of tsetse tissues and growth of trypanosomatids. *J. Protozool.* 24: 325-329.

Dennison S R, Wallace J, Harris F, Phoenix D A (2005) Amphiphilic α-helical antimicrobial peptides and their structure/function relationships. Protein Pept. Lett. 12: 31-9.

Giangaspero A, Sandri L, Tossi A (2001) Amphipathic a helical antimicrobial peptides: A systematic study of the effects of structural and physical properties on biological activity. Eur. J. Biochem. 268: 5589-600.

Hajdukiewicz P, Svab Z, Maliga P (1994) The small, versatile pPZP family of *Agrobacterium* binary vectors for plant transformation. Plant Mol. Biol. 25: 989-94.

Hooykaas P J J, Schilperoort R A (1992) *Agrobacterium* and plant genetic engineering. Plant Mol. Biol. 19: 15-38.

Isaacson T, Soto A, Iwamuro S, Knoop F C, Conlon J M (2002) Antimicrobial peptides with atypical structural features from the skin of the Japanese brown frog *Rana japonica*. Peptides 23: 419-25.

Kim J B, Iwamuro S, Knoop F C, Conlon J M (2001) Antimicrobial peptides from the skin of the Japanese mountain brown frog, *Rana ornativentris*. J. Pept. Res. 58: 349-56.

Kullmann W (1987) Enzymatic peptide synthesis, CRC Press, Florida.

Lemesre, J-L., D. Sereno, S. Daulouède, B. Veyret, N. Brajon, and P. Vincendeau. 1997. *Leishmania* spp.: nitric oxide-mediated metabolic inhibition of promastigote and axenically grown amastigote forms. Exp. Parasitol. 86: 58-68.

Mangoni M L (2006) Temporins, anti-infective peptides with expanding properties. Cell. Mol. Life Sci. 63: 1060-9.

Mosmann T (1983) Rapid colorimetric assay for cellular growth and survival: application to proliferation and cytotoxicity assays. J. Immunol. Methods 65: 55-63.

Rollins-Smith L A, Carey C, Conlon J M, Reinert L K, Doersam J K, Bergman T et al (2003) Activities of temporin family peptides against the chytrid fungus (*Batrachochytrium dendrobatidis*) associated with global amphibian declines. Antimicrob. Agents Chemother. 47: 1157-60.

Roy G, Dumas C, Sereno D, Wu Y, Singh A K, Tremblay M J, Ouellette M, Olivier M, Papadopoulou B (2000) Episomal and stable expression of the luciferase reporter gene for quantifying *Leishmania* spp. infections in macrophages and in animal models. Mol. Biochem. Parasitol. 110: 195-206.

Russell J A, Roy M K, Sanford J C (1992) Major improvements in biolistic transformation of suspension-cultured tobacco cells. In Vitro Cell. Dev. Biol., 28P, p. 97-105.

Sambrook J, Russell D (2001) Molecular cloning: a laboratory manual, Third Edition Cold Spring Harbor.

Sereno D, Lemesre J L (1997) Axenically cultured amastigote forms as an in vitro model for investigation of antileishmanial agents. Antimicrob. Agents Chemother. 41: 972-6.

Siemens, J, Schieder O (1996) Transgenic plants: genetic transformation—recent developments and the state of the art. Plant Tissue Cult. Biotechnol. 2: 66-75.

Simmaco M, De Biase G, Severini C, Aita M, Falconieri G, Erspamer, Barra D, Bossa F (1990) Purification and characterization of bioactive peptides from skin extract of *Rana esculenta*. Biochem. Biophys. Acta 1033: 318-23.

Simmaco M, Mignogna G, Canofeni S, Miele R, Mangoni M L, Barra D (1996) Temporins, antimicrobial peptides from the European red frog *Rana temporaria*. Eur. J. Biochem. 242: 788-92.

Vanhoye D, Bruston F, El Amri S, Ladram A, Amiche M, Nicolas P (2004) Membrane association, electrostatic sequestration and cytotoxicity of Gly-Leu-rich peptide orthologs with differing functions. Biochemistry 43: 8391-409.

Yeaman M R, Yount N Y (2003) Mechanisms of antimicrobial peptide action and resistance. Pharmacol. Rev. 55: 27-55.

SEQUENCE LISTING

<160> NUMBER OF SEQ ID NOS: 30

<210> SEQ ID NO 1
<211> LENGTH: 13
<212> TYPE: PRT
<213> ORGANISM: Pelophylax saharica

<400> SEQUENCE: 1

Phe Leu Ser Gly Ile Val Gly Met Leu Gly Lys Leu Phe
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Analog of temporin-SHa
<220> FEATURE:
<221> NAME/KEY: MISC_FEATURE
<222> LOCATION: (3)..(3)
<223> OTHER INFORMATION: X is X1 and represents R, H or K
<220> FEATURE:
<221> NAME/KEY: MISC_FEATURE
<222> LOCATION: (6)..(6)
<223> OTHER INFORMATION: X is X2 and represents V, R, H or K
<220> FEATURE:
<221> NAME/KEY: MISC_FEATURE
<222> LOCATION: (8)..(8)
<223> OTHER INFORMATION: X is X3 and represents M, R, H or K
<220> FEATURE:
<221> NAME/KEY: MISC_FEATURE
<222> LOCATION: (13)..(13)
<223> OTHER INFORMATION: X is X4 and represents F, L, I or W

<400> SEQUENCE: 2

Phe Leu Xaa Gly Ile Xaa Gly Xaa Leu Gly Lys Leu Xaa
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Analog of temporin-SHa

<400> SEQUENCE: 3

Phe Leu Lys Gly Ile Lys Gly Met Leu Gly Lys Leu Phe
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Analog of temporin-SHa

<400> SEQUENCE: 4

Phe Leu Lys Gly Ile Val Gly Lys Leu Gly Lys Leu Phe
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Analog of temporin-SHa

<400> SEQUENCE: 5

Phe Leu Lys Gly Ile Val Gly Met Leu Gly Lys Leu Leu

```
1               5                   10
```

<210> SEQ ID NO 6
<211> LENGTH: 13
<212> TYPE: PRT
<213> ORGANISM: Artificial Sequence
<220> FEATURE:
<223> OTHER INFORMATION: Analog of temporin-SHa

<400> SEQUENCE: 6

```
Phe Leu Lys Gly Ile Val Gly Met Leu Gly Lys Leu Trp
1               5                   10
```

<210> SEQ ID NO 7
<211> LENGTH: 13
<212> TYPE: PRT
<213> ORGANISM: Artificial Sequence
<220> FEATURE:
<223> OTHER INFORMATION: Analog of temporin-SHa

<400> SEQUENCE: 7

```
Phe Leu Lys Gly Ile Val Gly Met Leu Gly Lys Leu Ile
1               5                   10
```

<210> SEQ ID NO 8
<211> LENGTH: 13
<212> TYPE: PRT
<213> ORGANISM: Artificial Sequence
<220> FEATURE:
<223> OTHER INFORMATION: Analog of temporin-SHa

<400> SEQUENCE: 8

```
Phe Leu Lys Gly Ile Lys Gly Met Leu Gly Lys Leu Leu
1               5                   10
```

<210> SEQ ID NO 9
<211> LENGTH: 13
<212> TYPE: PRT
<213> ORGANISM: Artificial Sequence
<220> FEATURE:
<223> OTHER INFORMATION: Analog of temporin-SHa

<400> SEQUENCE: 9

```
Phe Leu Lys Gly Ile Lys Gly Met Leu Gly Lys Leu Trp
1               5                   10
```

<210> SEQ ID NO 10
<211> LENGTH: 13
<212> TYPE: PRT
<213> ORGANISM: Artificial Sequence
<220> FEATURE:
<223> OTHER INFORMATION: Analog of temporin-SHa

<400> SEQUENCE: 10

```
Phe Leu Lys Gly Ile Lys Gly Met Leu Gly Lys Leu Ile
1               5                   10
```

<210> SEQ ID NO 11
<211> LENGTH: 13
<212> TYPE: PRT
<213> ORGANISM: Artificial Sequence
<220> FEATURE:
<223> OTHER INFORMATION: Analog of temporin-SHa

<400> SEQUENCE: 11

```
Phe Leu Lys Gly Ile Val Gly Lys Leu Gly Lys Leu Trp
1               5                   10
```

```
<210> SEQ ID NO 12
<211> LENGTH: 13
<212> TYPE: PRT
<213> ORGANISM: Artificial Sequence
<220> FEATURE:
<223> OTHER INFORMATION: Analog of temporin-SHa

<400> SEQUENCE: 12

Phe Leu Lys Gly Ile Val Gly Lys Leu Gly Lys Leu Leu
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Analog of temporin-SHa

<400> SEQUENCE: 13

Phe Leu Lys Gly Ile Val Gly Lys Leu Gly Lys Leu Ile
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Analog of temporin-SHa

<400> SEQUENCE: 14

Phe Leu Lys Gly Ile Lys Gly Lys Leu Gly Lys Leu Phe
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Analog of temporin-SHa

<400> SEQUENCE: 15

Phe Leu Lys Gly Ile Lys Gly Lys Leu Gly Lys Leu Leu
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Analog of temporin-SHa

<400> SEQUENCE: 16

Phe Leu Lys Gly Ile Lys Gly Lys Leu Gly Lys Leu Trp
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Analog of temporin-SHa

<400> SEQUENCE: 17

Phe Leu Lys Gly Ile Lys Gly Lys Leu Gly Lys Leu Ile
1               5                   10
```

```
<210> SEQ ID NO 18
<211> LENGTH: 13
<212> TYPE: PRT
<213> ORGANISM: Artificial Sequence
<220> FEATURE:
<223> OTHER INFORMATION: Analog of temporin-SHa in which residues 3 and
      6 are substituted
<220> FEATURE:
<221> NAME/KEY: MISC_FEATURE
<222> LOCATION: (3)..(3)
<223> OTHER INFORMATION: X is X1 and represents R, H or K
<220> FEATURE:
<221> NAME/KEY: MISC_FEATURE
<222> LOCATION: (6)..(6)
<223> OTHER INFORMATION: X is X2 and represents R, H or K

<400> SEQUENCE: 18

Phe Leu Xaa Gly Ile Xaa Gly Met Leu Gly Lys Leu Phe
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Analog of temporin-SHa in which residues 3 and
      8 are substituted
<220> FEATURE:
<221> NAME/KEY: MISC_FEATURE
<222> LOCATION: (3)..(3)
<223> OTHER INFORMATION: X is X1 and represents R, H or K
<220> FEATURE:
<221> NAME/KEY: MISC_FEATURE
<222> LOCATION: (8)..(8)
<223> OTHER INFORMATION: X is X3 and represents R, H or K

<400> SEQUENCE: 19

Phe Leu Xaa Gly Ile Val Gly Xaa Leu Gly Lys Leu Phe
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Analog of temporin-SHa in which residues 3 and
      13 are substituted
<220> FEATURE:
<221> NAME/KEY: MISC_FEATURE
<222> LOCATION: (3)..(3)
<223> OTHER INFORMATION: X is X1 and represents R, H or K
<220> FEATURE:
<221> NAME/KEY: MISC_FEATURE
<222> LOCATION: (13)..(13)
<223> OTHER INFORMATION: X is X4 and represents I, L or W

<400> SEQUENCE: 20

Phe Leu Xaa Gly Ile Val Gly Met Leu Gly Lys Leu Xaa
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Analog of temporin-SHa in which residues 3, 6
      and 8 are substituted
<220> FEATURE:
<221> NAME/KEY: MISC_FEATURE
<222> LOCATION: (3)..(3)
<223> OTHER INFORMATION: X is X1 and represents R, H or K
<220> FEATURE:
```

```
<221> NAME/KEY: MISC_FEATURE
<222> LOCATION: (6)..(6)
<223> OTHER INFORMATION: X is X2 and represents R, H or K
<220> FEATURE:
<221> NAME/KEY: MISC_FEATURE
<222> LOCATION: (8)..(8)
<223> OTHER INFORMATION: X is X3 and represents R, H or K

<400> SEQUENCE: 21

Phe Leu Xaa Gly Ile Xaa Gly Xaa Leu Gly Lys Leu Phe
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Analog of temporin-SHa in which residues 3, 6
      and 13 are substituted
<220> FEATURE:
<221> NAME/KEY: MISC_FEATURE
<222> LOCATION: (3)..(3)
<223> OTHER INFORMATION: X is X1 and represents R, H or K
<220> FEATURE:
<221> NAME/KEY: MISC_FEATURE
<222> LOCATION: (6)..(6)
<223> OTHER INFORMATION: X is X2 and represents R, H or K
<220> FEATURE:
<221> NAME/KEY: MISC_FEATURE
<222> LOCATION: (13)..(13)
<223> OTHER INFORMATION: X is X4 and represents I, L or W

<400> SEQUENCE: 22

Phe Leu Xaa Gly Ile Xaa Gly Met Leu Gly Lys Leu Xaa
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Analog of temporin-SHa in which residues 3, 8
      and 13 are substituted
<220> FEATURE:
<221> NAME/KEY: MISC_FEATURE
<222> LOCATION: (3)..(3)
<223> OTHER INFORMATION: X is X1 and represents R, H or K
<220> FEATURE:
<221> NAME/KEY: MISC_FEATURE
<222> LOCATION: (8)..(8)
<223> OTHER INFORMATION: X is X3 and represents R, H or K
<220> FEATURE:
<221> NAME/KEY: MISC_FEATURE
<222> LOCATION: (13)..(13)
<223> OTHER INFORMATION: X is X4 and represents L, I or W

<400> SEQUENCE: 23

Phe Leu Xaa Gly Ile Val Gly Xaa Leu Gly Lys Leu Xaa
1               5                   10

<210> SEQ ID NO 24
<211> LENGTH: 50
<212> TYPE: PRT
<213> ORGANISM: Artificial Sequence
<220> FEATURE:
<223> OTHER INFORMATION: Precursor of analog of temporin-SHa
<220> FEATURE:
<221> NAME/KEY: MISC_FEATURE
<222> LOCATION: (38)..(38)
<223> OTHER INFORMATION: X is X1 and represents R, H or K
<220> FEATURE:
<221> NAME/KEY: MISC_FEATURE
<222> LOCATION: (41)..(41)
```

<223> OTHER INFORMATION: X is X2 and represents V, R, H or K
<220> FEATURE:
<221> NAME/KEY: MISC_FEATURE
<222> LOCATION: (43)..(43)
<223> OTHER INFORMATION: X is X3 and represents M, R, H or K
<220> FEATURE:
<221> NAME/KEY: MISC_FEATURE
<222> LOCATION: (48)..(48)
<223> OTHER INFORMATION: X is X4 and represents F, L, I or W

<400> SEQUENCE: 24

Phe Leu Gly Thr Ile Asn Leu Ser Leu Cys Glu Gln Glu Arg Asp Ala
1               5                   10                  15

Asp Glu Glu Glu Arg Arg Asp Glu Pro Asn Glu Ser Asn Val Glu Val
            20                  25                  30

Glu Lys Arg Phe Leu Xaa Gly Ile Xaa Gly Xaa Leu Gly Lys Leu Xaa
        35                  40                  45

Gly Lys
    50

<210> SEQ ID NO 25
<211> LENGTH: 12
<212> TYPE: PRT
<213> ORGANISM: Artificial Sequence
<220> FEATURE:
<223> OTHER INFORMATION: Analog of temporin-SHa in which residues 3
      and 6, 8 and/or 13 are substituted and wherein the sequence is
      shortened by one amino acid at the N-terminal end
<220> FEATURE:
<221> NAME/KEY: MISC_FEATURE
<222> LOCATION: (2)..(2)
<223> OTHER INFORMATION: X is X1 and represents R, H or K
<220> FEATURE:
<221> NAME/KEY: MISC_FEATURE
<222> LOCATION: (5)..(5)
<223> OTHER INFORMATION: X is X2 and represents V, R, H or K
<220> FEATURE:
<221> NAME/KEY: MISC_FEATURE
<222> LOCATION: (7)..(7)
<223> OTHER INFORMATION: X is X3 and represents M, R, H or K
<220> FEATURE:
<221> NAME/KEY: MISC_FEATURE
<222> LOCATION: (12)..(12)
<223> OTHER INFORMATION: X is X4 and represents F, L, I or W

<400> SEQUENCE: 25

Leu Xaa Gly Ile Xaa Gly Xaa Leu Gly Lys Leu Xaa
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Analog of temporin-SHa in which residues 3
      and 6, 8 and/or 13 are substituted and wherein the sequence is
      shortened by two amino acids at the N-terminal end
<220> FEATURE:
<221> NAME/KEY: MISC_FEATURE
<222> LOCATION: (1)..(1)
<223> OTHER INFORMATION: X is X1 and represents R, H or K
<220> FEATURE:
<221> NAME/KEY: MISC_FEATURE
<222> LOCATION: (4)..(4)
<223> OTHER INFORMATION: X is X2 and represents V, R, H or K
<220> FEATURE:
<221> NAME/KEY: MISC_FEATURE
<222> LOCATION: (6)..(6)
<223> OTHER INFORMATION: X is X3 and represents M, R, H or K
<220> FEATURE:
<221> NAME/KEY: MISC_FEATURE
<222> LOCATION: (11)..(11)

<223> OTHER INFORMATION: X is X4 and represents F, L, I or W

<400> SEQUENCE: 26

Xaa Gly Ile Xaa Gly Xaa Leu Gly Lys Leu Xaa
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Analog of temporin-SHa in which residues 3, 4,
      7 and/or 10 are substituted and wherein the sequence is shortened
      by two amino acids at the N-terminal end
<220> FEATURE:
<221> NAME/KEY: MISC_FEATURE
<222> LOCATION: (1)..(1)
<223> OTHER INFORMATION: X is X5 and represents S, R, H or K
<220> FEATURE:
<221> NAME/KEY: MISC_FEATURE
<222> LOCATION: (2)..(2)
<223> OTHER INFORMATION: X is X6 and represents G, R, H or K
<220> FEATURE:
<221> NAME/KEY: MISC_FEATURE
<222> LOCATION: (5)..(5)
<223> OTHER INFORMATION: X is X7 and represents G, R, H or K
<220> FEATURE:
<221> NAME/KEY: MISC_FEATURE
<222> LOCATION: (8)..(8)
<223> OTHER INFORMATION: X is X8 and represents G, R, H or K

<400> SEQUENCE: 27

Xaa Xaa Ile Val Xaa Met Leu Xaa Lys Leu Phe
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Analog of temporin-SHa in which residues 3, 4,
      7 and/or 10 are substituted and wherein the sequence is shortened
      by one amino acid at the N-terminal end
<220> FEATURE:
<221> NAME/KEY: MISC_FEATURE
<222> LOCATION: (2)..(2)
<223> OTHER INFORMATION: X is X5 and represents S, R, H or K
<220> FEATURE:
<221> NAME/KEY: MISC_FEATURE
<222> LOCATION: (3)..(3)
<223> OTHER INFORMATION: X is X6 and represents G, R, H or K
<220> FEATURE:
<221> NAME/KEY: MISC_FEATURE
<222> LOCATION: (6)..(6)
<223> OTHER INFORMATION: X is X7 and represents G, R, H or K
<220> FEATURE:
<221> NAME/KEY: MISC_FEATURE
<222> LOCATION: (9)..(9)
<223> OTHER INFORMATION: X is X8 and represents G, R, H or K

<400> SEQUENCE: 28

Leu Xaa Xaa Ile Val Xaa Met Leu Xaa Lys Leu Phe
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Analog of temporin-SHa

<400> SEQUENCE: 29

```
Phe Leu Lys Gly Ile Val Gly Met Leu Gly Lys Leu Phe
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Analog of temporin-SHa

<400> SEQUENCE: 30

Lys Gly Ile Val Gly Met Leu Gly Lys Leu Phe
1               5                   10
```

The invention claimed is:

1. A peptide of a size comprised between 13 and 100 amino acids exhibiting an antimicrobial activity, said antimicrobial activity being an antibacterial activity, an antifungal activity against a fungus from the genus *Candida*, and/or an antiparasitic activity against a parasite from the genus *Leishmania*, and comprising the sequence F-L-$X_1$-G-I-$X_2$-G-$X_3$-L-G-K-L-$X_4$ (SEQ ID NO: 2), wherein:

$X_1$ is an amino acid selected from the group consisting of R, H and K, $X_2$ is an amino acid selected from the group consisting of V, R, H and K, $X_3$ is an amino acid selected from the group consisting of M, R, H and K, and $X_4$ is an amino acid selected from the group consisting of F, I, L and W, with the proviso that when $X_2$ is V, then $X_3$ is selected from the group consisting of K, R and H and/or $X_4$ is selected from the group consisting of L, I and W, and the pharmaceutically acceptable salts of said peptide.

2. The peptide according to claim 1, wherein $X_1$ represents K, $X_2$ is an amino acid selected from the group consisting of V and K, $X_3$ is an amino acid selected from the group consisting of M and K, and $X_4$ is an amino acid selected from the group consisting of F, L and W.

3. The peptide according to claim 1, wherein the peptide comprises a sequence selected from the group consisting of SEQ ID NOs: 3 to 17.

4. A nucleic acid encoding a peptide according to claim 1.

5. An expression cassette comprising a nucleic acid according to claim 4.

6. An expression vector comprising a nucleic acid according to claim 4.

7. A host cell comprising a nucleic acid according to claim 4.

8. A pharmaceutical composition comprising at least one peptide according to claim 1 and a pharmaceutically acceptable support and/or excipient.

9. A method of treating a microbial infection comprising administering a peptide according to claim 1 to a subject having a microbial infection, wherein the microbial infection is a bacterial infection, a fungal infection by a fungus from the genus *Candida*, or a parasitic infection by a parasite from the genus *Leishmania*.

10. The method according to claim 9, wherein said microbial infection is an infection caused by a bacterium.

11. The method according to claim 9, wherein said microbial infection is an infection caused by a parasite from the genus *Leishmania*.

12. A medical device or implant comprising a body having at least one surface coated with or including a peptide according to claim 1.

13. A transgenic plant comprising a nucleic acid according to claim 4.

14. The peptide of claim 1, wherein the peptide comprises a sequence selected from the group consisting of SEQ ID NOs: 3, 4, 5, 6 and 8.

15. The peptide of claim 1, wherein the peptide consists of a sequence selected from the group consisting of SEQ ID NOs: 3, 4, 5, 6 and 8.

16. The method of claim 9, wherein the microbial infection is a fungal infection by a fungus from the genus *Candida*.

17. The method of claim 16, wherein the fungus is *Candida albicans* or *Candida parapsilosis*.

18. The method of claim 11, wherein the parasite is *Leishmania infantum*.

19. The method of claim 10, wherein the bacterium is a Gram negative bacterium.

20. The method of claim 10, wherein the bacterium is a Gram positive bacterium.

21. The method of claim 19, wherein the Gram negative bacterium is selected from the group consisting of *Escherichia coli* and bacteria from the genera *Pseudomonas*, *Salmonella*, *Acinetobacter* and *Klebsiella*.

22. The method of claim 20, wherein the Gram positive bacterium is selected from the group consisting of bacteria from the genera *Staphylococcus*, *Streptococcus*, *Listeria* and *Enterococcus*.

* * * * *

UNITED STATES PATENT AND TRADEMARK OFFICE
CERTIFICATE OF CORRECTION

PATENT NO.       : 9,932,376 B2
APPLICATION NO.  : 15/021948
DATED            : April 3, 2018
INVENTOR(S)      : Ali Ladram et al.

It is certified that error appears in the above-identified patent and that said Letters Patent is hereby corrected as shown below:

In the Specification

Column 4,
Line 48, "an a helical" should read --an α helical--.
Line 55, "22.8 respectively" should read --22.8 µM, respectively--.
Line 56, "AMPS is" should read --AMPs is--.

Column 8,
Line 17, "$X_5$-(SEQ ID NO: 27)" should read --$X_5$-$X_6$-I-V-$X_7$-M-L-$X_8$-K-L-F (SEQ ID NO: 27)--.

Column 18,
Line 15, "50 of PBS" should read --50 µL of PBS--.

Column 20,
Line 53, "($LC_{50}$>500 µM They" should read --($LC_{50}$ > 500 µM). They--.

Column 22,
Lines 1-2, "Amphipathic a helical" should read --Amphipathic α helical--.

Signed and Sealed this
Twenty-third Day of April, 2019

Andrei Iancu
*Director of the United States Patent and Trademark Office*